US012376786B2

(12) United States Patent
Uthoff et al.

(10) Patent No.: US 12,376,786 B2
(45) Date of Patent: Aug. 5, 2025

(54) SMARTPHONE-BASED MULTISPECTRAL DERMASCOPE

(71) Applicant: Arizona Board of Regents on Behalf of the University of Arizona, Tucson, AZ (US)

(72) Inventors: Ross Uthoff, Seattle, WA (US); Rongguang Liang, Tucson, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 139 days.

(21) Appl. No.: 18/248,479

(22) PCT Filed: Oct. 8, 2021

(86) PCT No.: PCT/US2021/054129
§ 371 (c)(1),
(2) Date: Apr. 10, 2023

(87) PCT Pub. No.: WO2022/076792
PCT Pub. Date: Apr. 14, 2022

(65) Prior Publication Data
US 2023/0371885 A1    Nov. 23, 2023

Related U.S. Application Data

(60) Provisional application No. 63/090,102, filed on Oct. 9, 2020.

(51) Int. Cl.
*A61B 5/00* (2006.01)

(52) U.S. Cl.
CPC ............ *A61B 5/444* (2013.01); *A61B 5/0075* (2013.01); *A61B 5/0077* (2013.01); *A61B 5/6898* (2013.01)

(58) Field of Classification Search
CPC ..... A61B 5/444; A61B 5/0075; A61B 5/0077; A61B 5/6898; A61B 5/7475; A61B 5/748;
(Continued)

(56) References Cited

U.S. PATENT DOCUMENTS 10,678,120 B1 *   6/2020   Lozano-Buhl ............ H01F 7/02
11,003,048 B1 *   5/2021   Rawlani ............... A61B 5/0077
(Continued)

OTHER PUBLICATIONS

International Search Report and Written Opinion mailed Jan. 14, 2022 for International Patent Application No. PCT/US21/54129.
(Continued)

*Primary Examiner* — Adil Partap S Virk
(74) *Attorney, Agent, or Firm* — Perkins Coie LLP

(57) ABSTRACT

Methods, apparatus and systems that relate to a portable multispectral dermascope are described. An example dermascope includes light sources having different spectral contents and configured to illuminate an area of the skin and at least one imaging sensor configured to collect light that it receives from the area of the skin. The dermascope also includes a processor to control illumination provided by the light sources to the area of the skin and process information associated with received light from the area of the skin to produce images of the area of the skin. In the dermascope, illumination from the light sources is controlled to provide illumination in a plurality of distinct wavelengths or range of wavelengths that produce differing optical responses of the area of the skin. The described methods and devices can be used to identify skin conditions using a compact and convenient device, such as a mobile phone.

24 Claims, 22 Drawing Sheets

(58) Field of Classification Search
CPC .......... A61B 2560/0431; A61B 5/0084; A61B 5/0013; A61B 5/0071; A61B 5/414; A61B 5/441; A61B 5/4836; A61B 5/726; A61B 2560/0233; G06T 7/0012; G06T 2207/30088; G06T 2207/30096; G01B 11/26; G01S 17/08; G01J 3/0218; G01J 3/443; G01J 3/28; G01N 21/718; G16H 50/20

See application file for complete search history.

(56) References Cited

U.S. PATENT DOCUMENTS

| | | | |
|---|---|---|---|
| 11,116,407 B2* | 9/2021 | Dickie | H04N 5/265 |
| 12,137,979 B2* | 11/2024 | Tran | A61B 3/107 |
| 2003/0045799 A1* | 3/2003 | Bazin | G01N 21/84 |
| | | | 600/476 |
| 2010/0292549 A1* | 11/2010 | Shuler | A61B 5/14552 |
| | | | 600/324 |
| 2014/0066727 A1 | 3/2014 | Heine et al. | |
| 2015/0025343 A1* | 1/2015 | Gareau | A61B 5/14552 |
| | | | 600/328 |
| 2016/0166194 A1* | 6/2016 | Gareau | A61B 5/14552 |
| | | | 600/328 |
| 2016/0239960 A1* | 8/2016 | Byers | G06F 18/22 |
| 2017/0119250 A1* | 5/2017 | Kolachalama | A61B 3/14 |
| 2017/0303857 A1* | 10/2017 | Perkins | H04N 7/185 |
| 2018/0140196 A1* | 5/2018 | Khosravi Simchi | A61B 90/36 |
| 2019/0038135 A1* | 2/2019 | Lee | A61B 3/12 |
| 2019/0216402 A1* | 7/2019 | Sayani | A61B 1/233 |
| 2019/0343396 A1* | 11/2019 | Khosravi Simchi | |
| | | | G03B 17/565 |
| 2019/0350513 A1 | 11/2019 | Carrein et al. | |
| 2023/0189964 A1* | 6/2023 | Du | A61B 5/7435 |
| | | | 132/200 |

OTHER PUBLICATIONS

Uthoff, Ross D., et al., "Point-of-care, multispectral, smartphone-based dermascopes for dermal lesion screening and erythema monitoring," Journal of Biomedical Optics vol. 25(6), 2020.

* cited by examiner

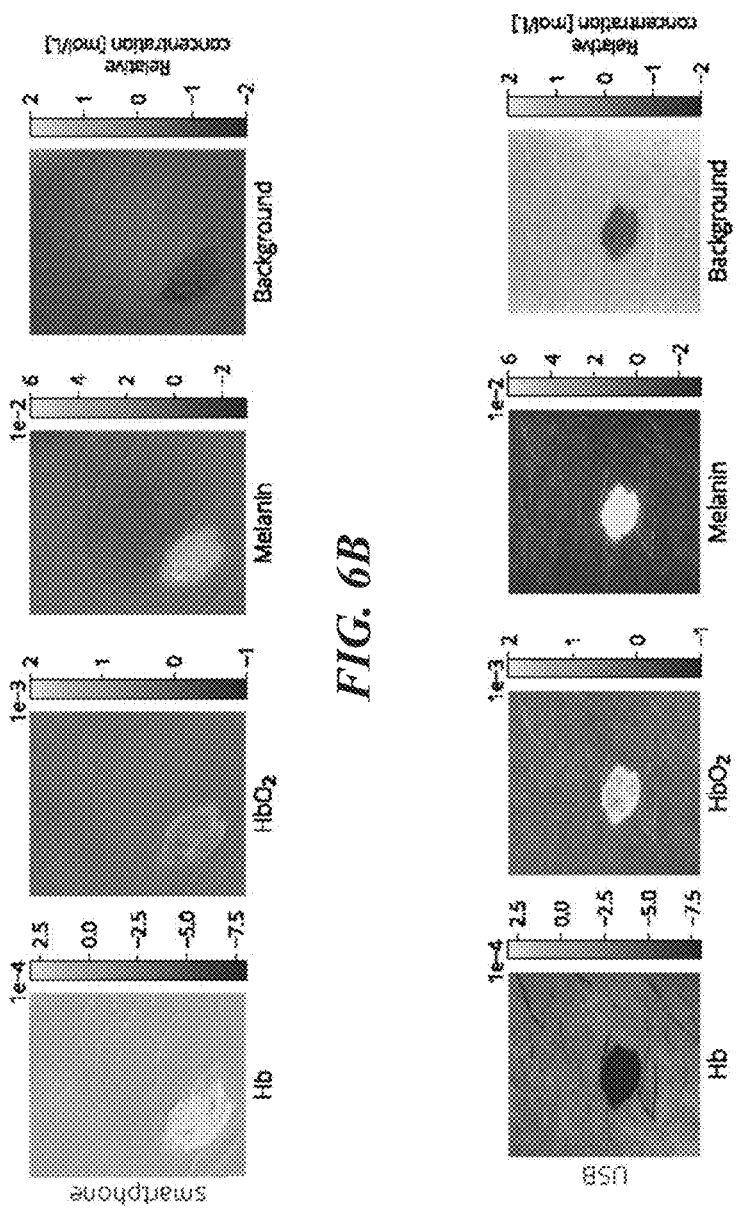
*FIG. 6B*
*FIG. 6C*
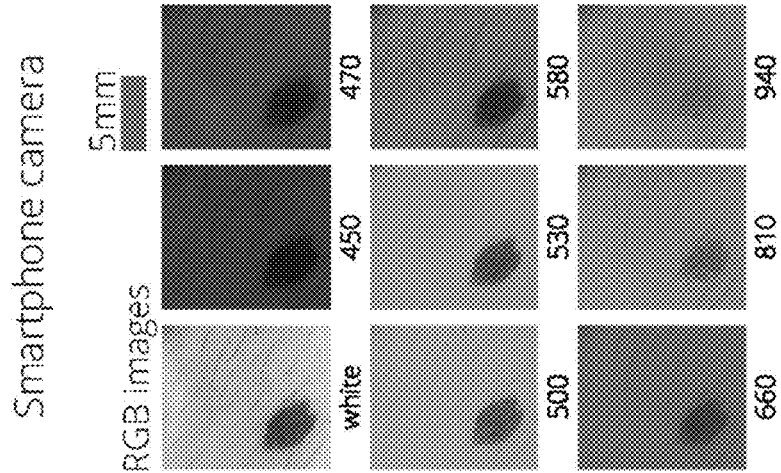
*FIG. 6A*

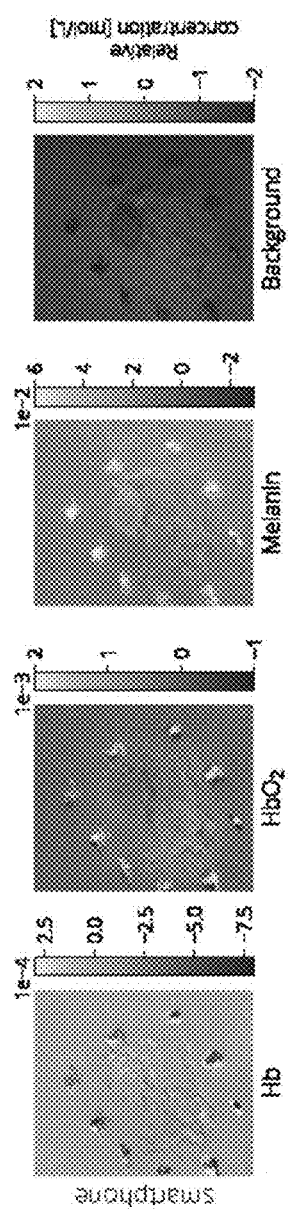
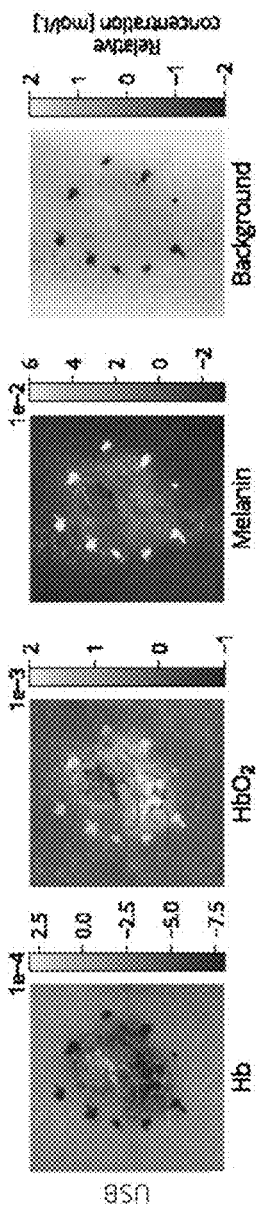
*FIG. 7B*
*FIG. 7C*
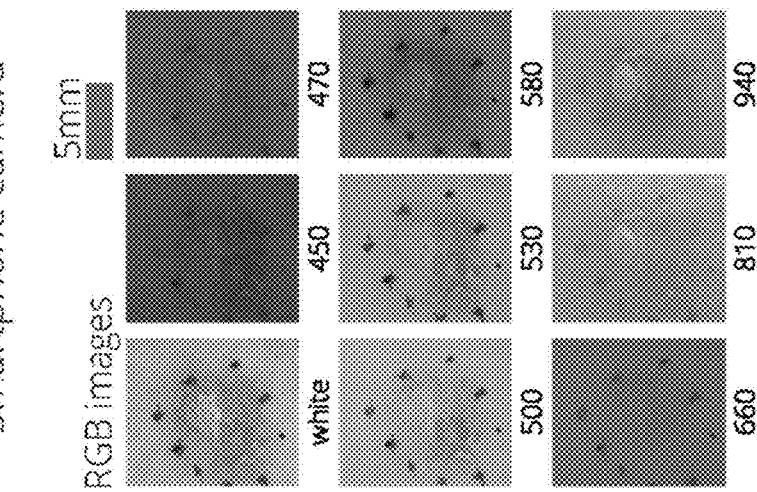
*FIG. 7A*

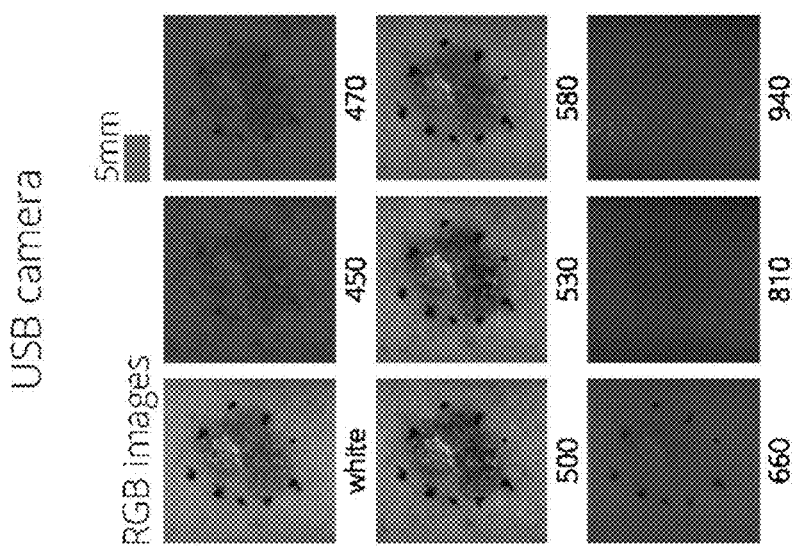
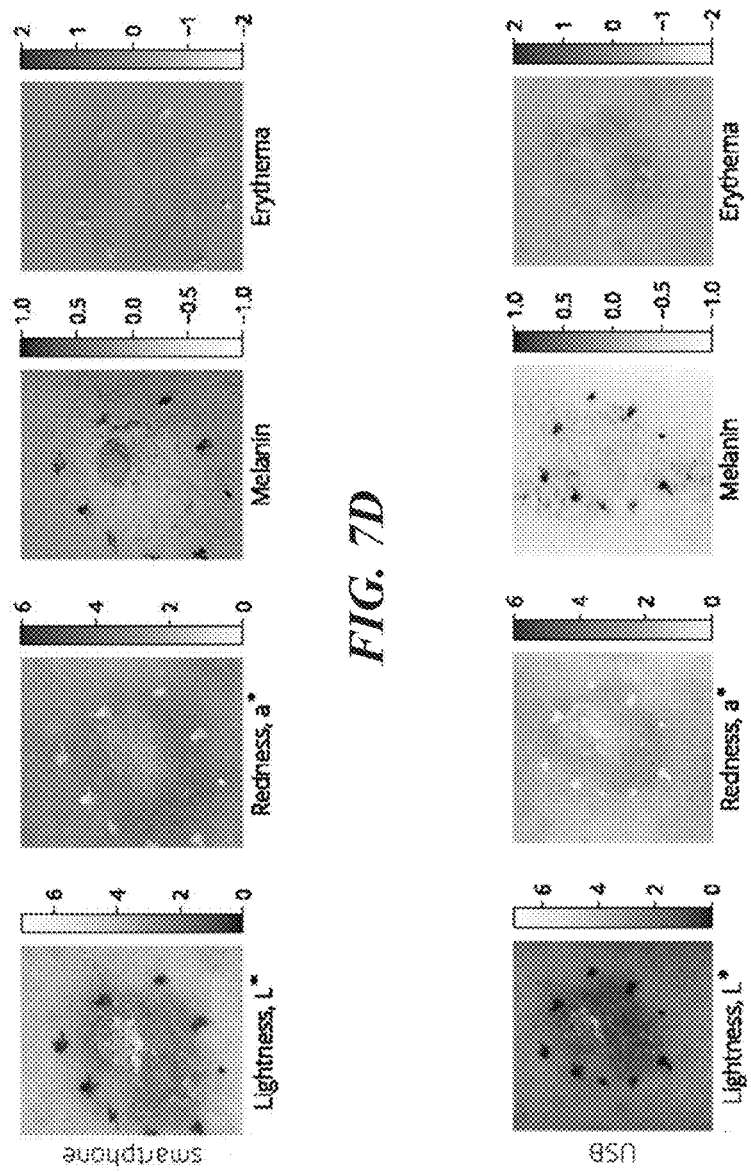
FIG. 7D
FIG. 7E
FIG. 7F

SMARTPHONE-BASED MULTISPECTRAL DERMASCOPE

RELATED APPLICATIONS

This patent document is a 371 National Phase Application of International Patent Application No. PCT/US2021/054129, filed Oct. 8, 2021, which claims priority to and benefits of U.S. Provisional Patent Application No. 63/090,102 entitled "SMARTPHONE-BASED MULTISPECTRAL DERMASCOPE" and filed on Oct. 9, 2020. The entire contents of the before-mentioned patent applications are incorporated by reference as part of the disclosure of this patent document.

STATEMENT REGARDING FEDERALLY SPONSORED RESEARCH

This invention was made with government support under Grant No. EB000809, and Grant No. OD018061, awarded by the National Institutes of Health. The government has certain rights in the invention.

TECHNICAL FIELD

The disclosed technology relates generally to optical methods and devices which can facilitate identification of various skin conditions and, more specifically, to portable dermascope devices in some embodiments.

BACKGROUND

Dermoscopy is an in vivo technique which is primarily used for the examination of pigmented skin lesions. Dermoscopy can be used to differentiate between benign and malignant lesions. Currently, dermascopes and their accessories range from hundreds to thousands of dollars in price, which is potentially too expensive for general medical practices. Accordingly, there is still a need to produce a low-cost hand-held dermascope device.

SUMMARY OF CERTAIN EMBODIMENTS

The techniques disclosed herein can be implemented in various embodiments to achieve a portable (e.g., a mobile device based) multispectral dermascope.

An aspect of the disclosed embodiments relates to a dermascope for imaging an area of a skin that includes a plurality of light sources having different spectral contents and configured to illuminate the area of the skin. The dermascope further includes at least one imaging sensor configured to collect images of the area of the skin. The dermascope also includes a processor and a memory comprising instructions stored thereon, wherein the instructions upon execution by the processor, cause the processor to control illumination provided by the plurality of light sources to the area of the skin, and process information associated with the images produced from reflected light from the area of the skin to enable detection of a level of one or more chromophores in the skin, wherein illumination from the plurality of light sources is controlled to provide illumination in a plurality of distinct wavelengths or range of wavelengths where the one or more chromophores exhibit differing optical characteristics.

Another aspect of the disclosed embodiments relates to a method of imaging an area of a skin to determine a content of at least one chromophore in the skin that includes illuminating the area of the skin using a plurality of light sources having distinct spectral content to provide illumination in a plurality of distinct wavelengths or range of wavelengths where deoxyhemoglobin, oxyhemoglobin, or melanin exhibit differing optical characteristics. The method also includes obtaining one or more images of the area of the skin. The method further includes processing information associated with the one or more images to obtain a level of at least one chromophore in the skin.

BRIEF DESCRIPTION OF THE DRAWINGS

FIGS. 6A-6F illustrate RGB, chromophore, melanin, and erythema measures for a case of junctional nevus (JN) obtained using a USB camera dermascope and a smartphone camera dermascope according to the disclosed technology.

FIGS. 7A-7F illustrate RGB, chromophore, melanin, and erythema measures for a case of squamous cell carcinoma (SCC) obtained using a USB camera dermascope and a smartphone camera dermascope according to the present disclosure.

DETAILED DESCRIPTION

Figure 1B:
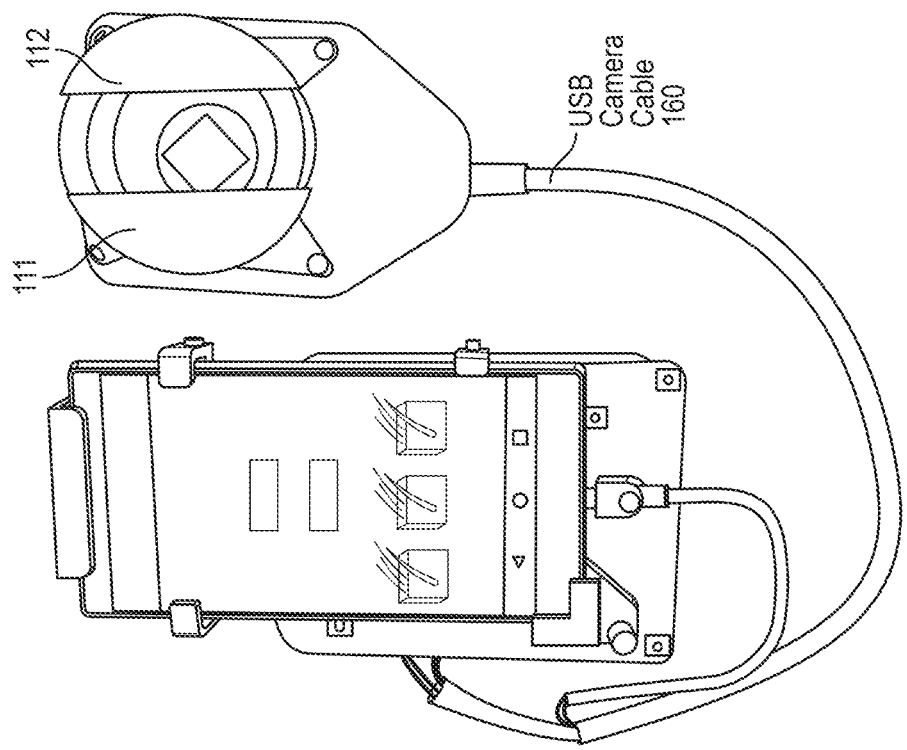
FIGS. 1A-1E illustrate two smartphone-based dermascope system configurations in accordance with example embodiments.

The techniques disclosed herein overcome the shortcomings of prior systems and can be implemented in various embodiments to provide a low-cost handheld dermascope. The disclosed devices and systems, among other features and benefits, address the need for low-cost, handheld imaging systems that can be used for detecting and diagnosing skin conditions such as, e.g., melanoma or erythema.

The rates of melanoma and nonmelanoma skin cancers (NMSC) have been steadily rising, and early diagnosis is key for improved outcomes. Because there is a shortage of board-certified dermatologists, particularly in remote or underserved settings where <10% of dermatologists practice, most of the burden of diagnosis and treatment falls on primary care physicians (PCPs) who are not extensively trained in dermatological care. Dermoscopy is a tool utilized to improve the in vivo diagnostic accuracy of benign versus malignant lesions, a unique skill that requires additional training, even among board-certified dermatologists. In remote settings, dermascopes may capture and document pigmented lesions that can be forwarded to expert colleagues through telemedicine for further analysis. Unfortunately, dermascopes and their accessories range from hundreds to thousands of dollars, which is potentially too expensive for general medical practice. Thus, there is a need for a low-cost, readily available dermoscopy tool to bridge this clinical need.

Lesion evaluation using visual, subjective methods such as the ABCDE criteria and seven-point checklist are useful tools for PCPs. The ABCDE criteria predict melanoma by a lesion's asymmetry, border irregularity, coloration, diameter if >6 mm, and evolution, providing a sensitivity of 0.85 and specificity of 0.72. The seven-point checklist monitors a lesion's change in size, shape, color, and looks for diameters >7 mm, crusting or bleeding, and sensory change, providing a sensitivity of 0.77 and specificity of 0.80. Continuous monitoring has shown to improve outcomes through early detection as evidenced by mole mapping techniques and the increase in sensitivity and specificity with the addition of the evolving in the ABCDE criteria.

Adjunctive tools utilizing objective measures such as polarized multispectral imaging (PMSI) and polarized white-light imaging (PWLI) to map dermal chromophores (e.g., hemoglobin, oxyhemoglobin ($HbO_2$), deoxyhemoglobin (Hb), and/or melanin), quantify erythema, and perform image classification for lesion screening have the potential to increase early detection of melanoma by PCPs and even outside the physician's office, leading to reduced need for biopsy and improved outcomes. Disclosed herein are systems and devices that utilize a mobile electronic device (e.g., a smartphone, a tablet, or the like) combined with LED illumination as the platform for an adjunctive medical device. The disclosed devices provide a portable system with easy-to-operate apps and native image capture, processing, and data transmission capabilities. These systems can reduce the costs associated with interference-filter-based or spectrometer-based systems while also providing a more compact, portable geometry for use in any testing environment compared with clinical-grade imaging systems.

Disclosed herein are two example point-of-care dermascope configurations for skin lesion screening and erythema monitoring, implementing both PMSI and PWLI on an LG G5 (LG, Seoul, South Korea) smartphone platform. These configurations are provided by the way of example, and not by limitation, to illustrate the principles of operation of the disclosed dermascope. One example system utilizes the embedded smartphone camera for imaging while the other example system uses a USB-connected camera module that connects to the smartphone. Both systems share a common illumination system and software application to enable PWLI and PMSI.

Figure 1A:
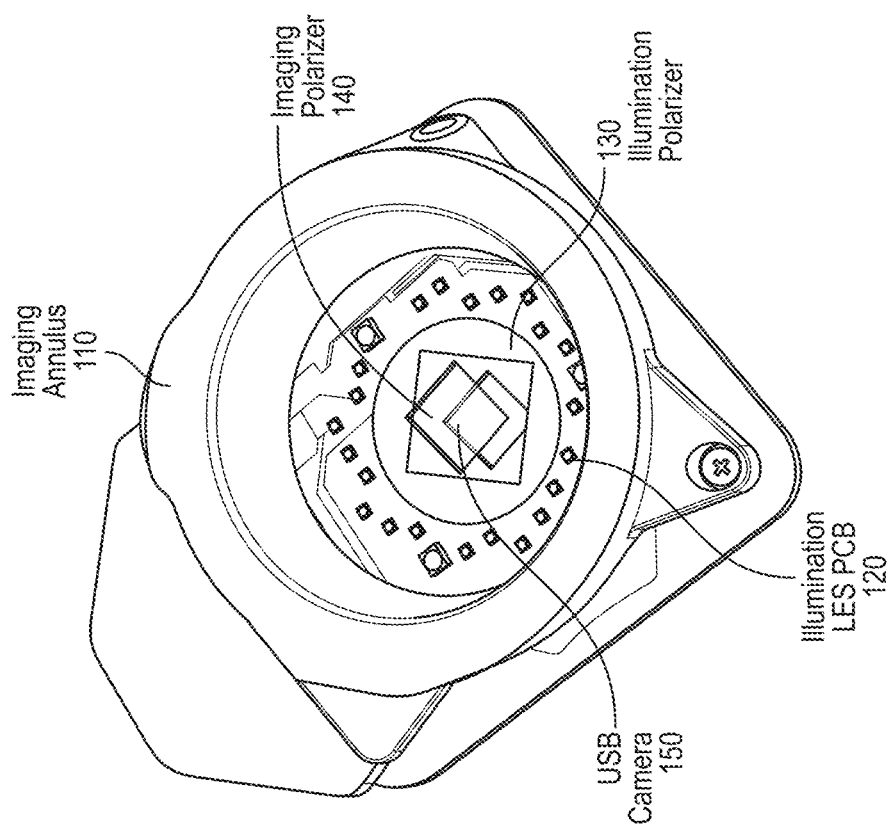
Figure 1C:
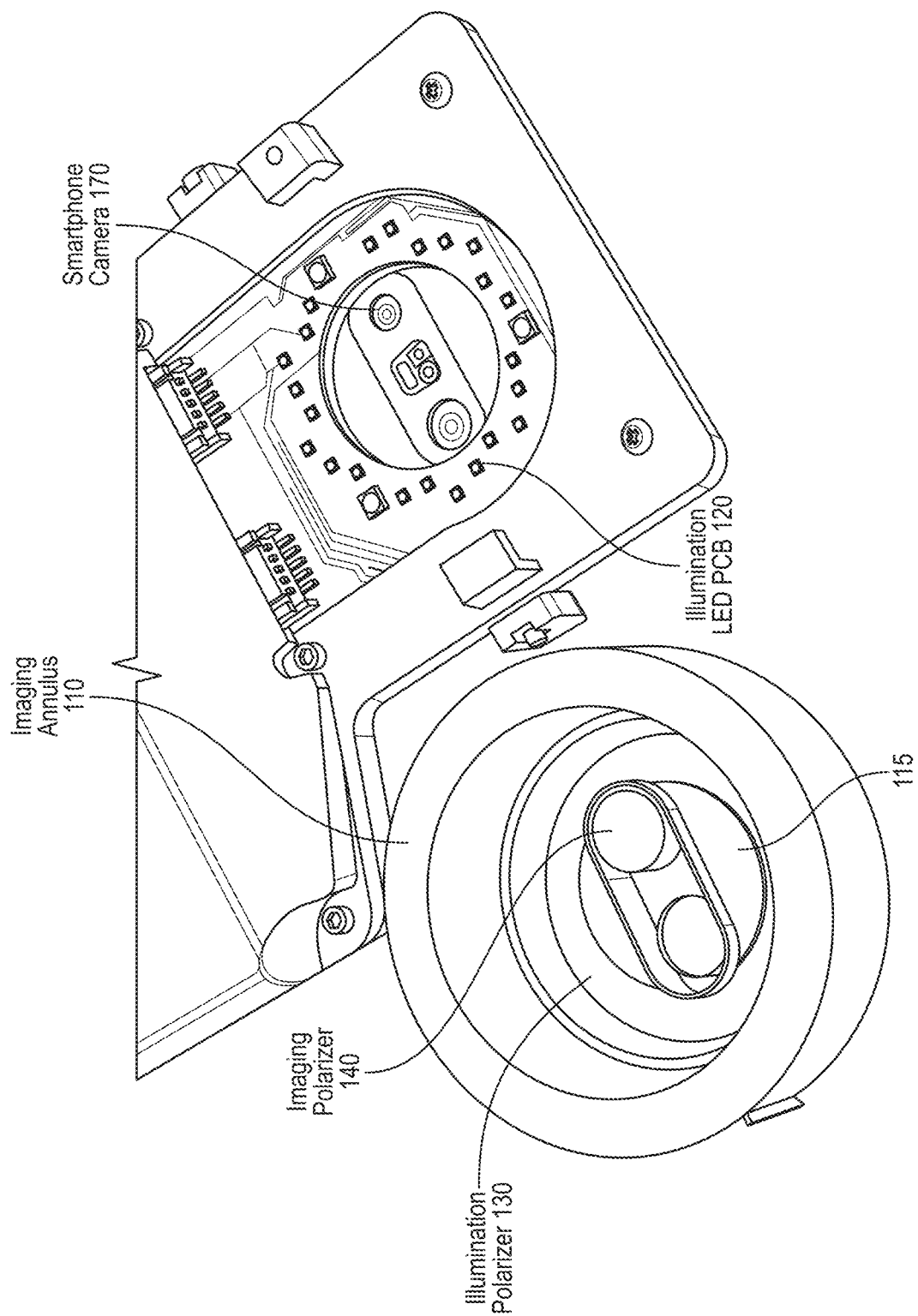
Figure 1E:
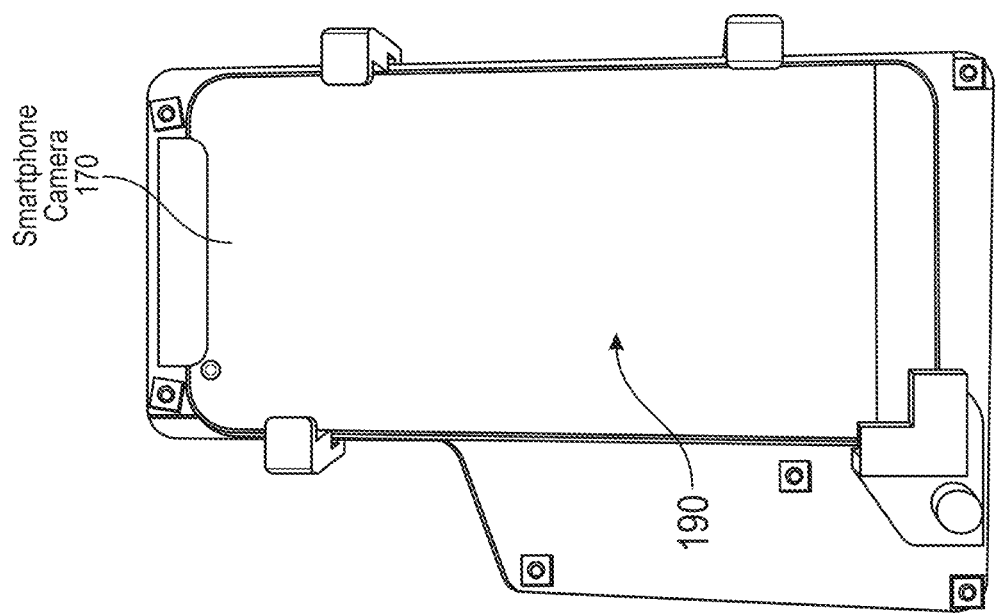
Figure 1D:
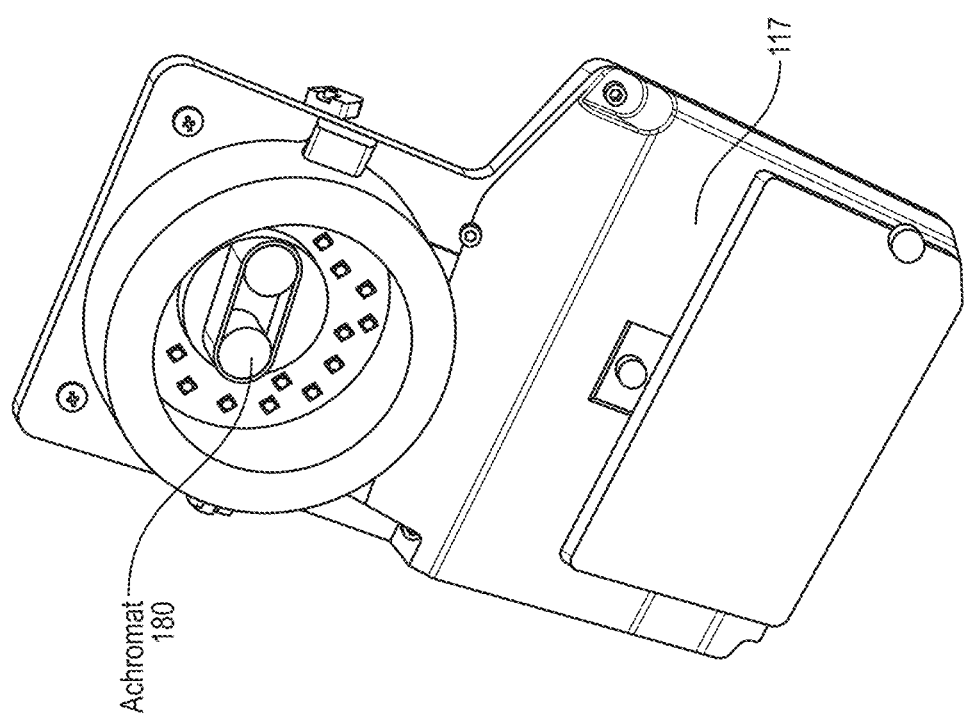

Two example PMSI and PWLI dermascope systems which use the smartphone's embedded rear camera are shown in FIGS. 1C-1E. The main LG G5 camera (170 in FIGS. 1C and 1E) includes a Sony IMX234 Exmor RS sensor with 5312×2988, 1.12-µm pixels and a 5.95 mm×3.35 mm sensor size. The sensor is paired with a f/1.8, 4.42-mm focal length lens.

Figure 2:
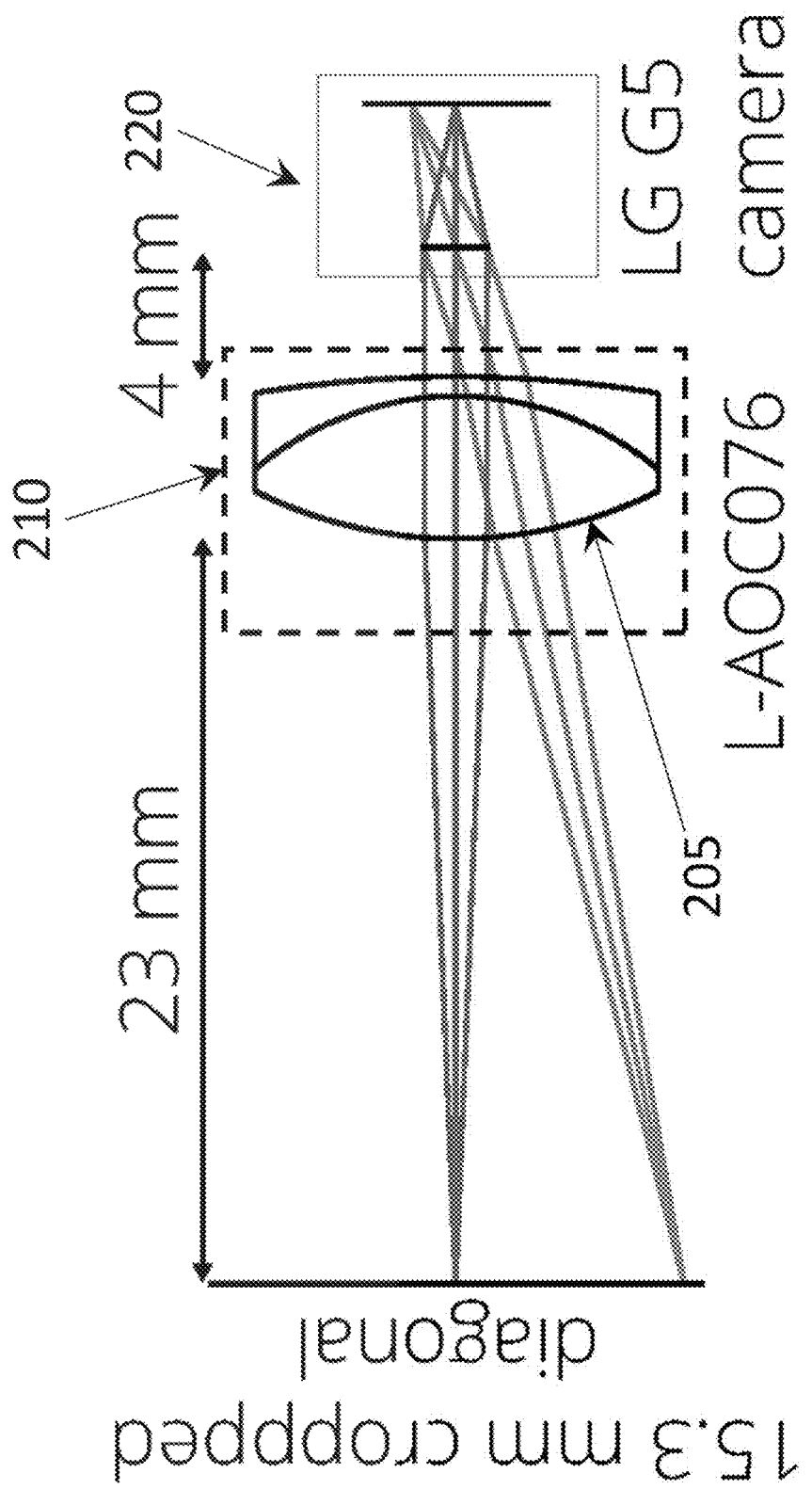
FIG. 2 illustrates a layout of a smartphone camera and an achromat which is part of an auxiliary optical system at the front end of a smartphone in accordance with an example embodiment.

To decrease the working distance of the optical system to allow imaging of the epidermis, a 24-mm focal length achromatic doublet (180 in FIG. 1D; Ross Optical, El Paso, Texas, USA) is placed 4 mm away from the principal plane of the smartphone optical system, providing a magnification of m=0.187 and a numerical aperture NA=0.04. After cropping, the field of view (FOV) is 9.96 mm×11.67 mm, as shown in FIG. 2. It should be noted that the configuration of FIG. 2 is only provided as an example, and other auxiliary optical systems can be designed and constructed to provide the desired FOV, numerical apertures, magnification, zoom capability and/or working distance for the particular electronic mobile device and/or for different applications that may have particular imaging requirements. As shown in FIG. 2, the imaging achromat 205 (which can be part of the auxiliary optical system 210) can be aligned to the smartphone camera (220 in FIG. 2) using, for example, a machined poly(methyl methacrylate) (PMMA) disk (115 in FIG. 1C) installed in a removable 3D-printed annulus (110 in FIG. 1C) made of, e.g., VeroBlue RGD840 (Stratasys, Eden Prairie, Minnesota, USA) plastic. The annulus 110 (see, e.g., FIGS. 1A and 1C) serves as an imaging guide. Its length can equal to the optical system working distance (23 mm), so the PCP can contact the patient to stabilize the device and ensure correct focus. An additional 3D-printed structure (117 in FIG. 1D) serves as a mounting platform for the smartphone (e.g., smartphone 190 shown in FIG. 1E), imaging annulus, and LED electronics (e.g., illumination LED printed circuit board (PCB) 120 shown in FIGS. 1A and 1C). In some implementations, a transparent piece of glass or plastic can be placed at the end of the annulus to flatten the skin (e.g., in the non-3D mode) to make the object plane (the skin) flat for better imaging. This feature can also facilitate the sterilization of the device. It should be noted that the auxiliary optical system can include mirrors, metasurfaces, metalenses, or diffractive optics to obtain the desired performance characteristics.

An alternative PMSI and PWLI dermascope example configuration illustrated in FIGS. 1A and 1B is also based on an LG smartphone platform, but it utilizes an external USB-connected RGB camera 150 (e.g., OV5648, Omnivision, Santa Clara, California, USA; 5 MP, 3.67 mm×2.74 mm) with the vendor-supplied ~2.8-mm focal length lens adjusted to a working distance of 30 mm. The camera 150 shown in FIG. 1A can be connected to a smartphone using, e.g., a USB cable 160 shown in FIG. 1B. After cropping, the FOV is 27.5 mm×20 mm. In addition, the integrated infrared (IR) filter of the camera 150 was removed to allow illumination and capture of IR light that can be particularly beneficial for skin imaging. Again, the mechanical design of the annulus is matched to the working distance of the camera, providing in-focus imaging when the device contacts the patient.

As noted above, FIGS. 1A-1E illustrate two example dermascope implementations. The USB-camera-based PMSI and PWLI dermascope is shown in FIGS. 1A and 1B. FIG. 1A illustrates various components of the handheld imaging module (the USB camera 150 is hidden behind the imaging polarizer 140). FIG. 1B illustrates the imaging module paired with the smartphone camera. LEDs are positioned on the illumination LED PCB 120 to provide illumination toward the skin (toward the open end of the annulus). A Polarization filter (e.g., the illumination polarizer 130 shown in FIGS. 1A and 1C) can be positioned in front the light sources to produce polarized light having a particular polarization state. Upon reflection from the skin, the reflected light is received and collected by the camera lens. Another polarization filter (e.g., the imaging polarizer 140 shown in FIGS. 1A and 1C) can be placed in path of the reflected light to reduce stray light contamination. The image data (or associated electrical signals) corresponding to the images is received at the smartphone, and is stored, processed and/or transmitted to a remote device for processing/storage.

An example smartphone-camera-based PMSI and PWLI dermascope is shown in FIGS. 1C-1E. FIG. 1C illustrates the smartphone-based dermascope system's side opposite the smartphone screen with the imaging annulus 110 removed, where the LED PCB 120 and smartphone camera 170 are visible and other components are highlighted. FIG. 1D illustrates the dermascope system with the imaging annulus attached. FIG. 1E illustrates the smartphone installed in the dermascope.

FIG. 2 illustrates a layout of a smartphone camera 220 (e.g., a camera of an LG G5 smartphone) and an achromat 205 which is part of an auxiliary optical system 210 at the front end of the smartphone, according to an example embodiment. The smartphone camera lens system can be modeled as a paraxial lens, which simplifies the design of the front-end system.

Figure 3:
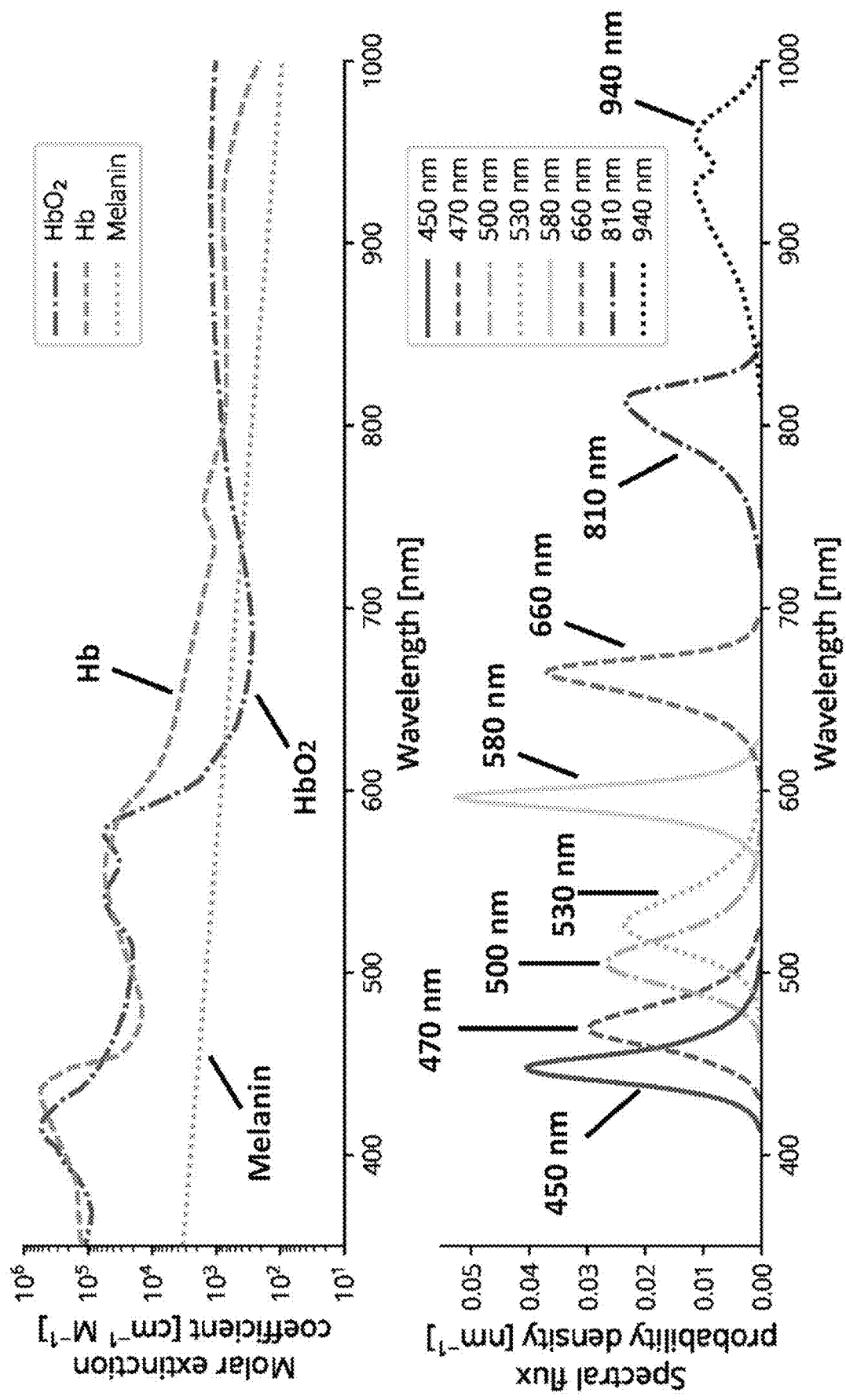
FIG. 3 illustrates example molar extinction coefficients, $\varepsilon(\lambda)$, for oxyhemoglobin, deoxyhemoglobin and melanin as well as light-emitting diode (LED) spectral flux probability density functions, $\phi_{e,\lambda}$, according to the present disclosure.

For both example dermascope systems illustrated in FIGS. 1A-1E, multispectral illumination can be accomplished using a custom printed circuit board (e.g., the board 120 shown in FIGS. 1A and 1C) with LEDs of various wavelengths (e.g., Lumileds, Amsterdam, The Netherlands or Vishay, Malvern, Pennsylvania, USA) installed as, e.g., shown in Table 1. In some example embodiments, the color wavelengths can be chosen based on the ability to probe both hemoglobin isosbestic points and separate oxygenated from deoxygenated hemoglobin content along the molar attenuation curves (FIG. 3).

According to some example embodiments of the smartphone-based dermascope, the PMMA disk 115 used for mounting a lens (e.g., the imaging achromat 180 shown in FIG. 1D) or, more generally, for mounting the auxiliary optical system 210 also extends over the illumination LEDs to provide mounting for a polarizer (e.g., a linear polarizer; Edmund Optics, Barrington, New Jersey, USA) such as the illumination polarizer 130 shown in FIGS. 1A and 1C. An orthogonal linear polarizer (e.g., the imaging polarizer 140) can be installed in front of the imaging channel, enabling both PMSI and PWLI and reducing the effect of specular reflection on the images. The LED sources' spectral fluxes, $\phi_{e,\lambda}$, shown in the lower panel in FIG. 3, were measured with a spectrometer (Ocean Optics).

The example USB-camera-based dermascope illustrated in FIGS. 1A and 1B uses the same LED PCB 120 and wavelengths for illumination along with orthogonal polarizers in the illumination channel (130; Edmund Optics) and the imaging channel (140; Moxtek, Orem, Utah, USA). In some example embodiments, to help normalize white-light image luminance, an 18% gray color reference (e.g., Kodak, Rochester, New York, USA) can be installed on both sides of the image FOV. Because the 3D-printed mounting foundation does not need to mount the LED board and imaging annulus, a previously designed geometry is used for this system.

Table 1 provides a listing of LED and camera settings for each illumination wavelength and each dermascope. LED wavelength (λ), LED part number, smartphone camera LED-driving current (l), smartphone camera LED flux for a single LED of the given color, smartphone camera International Organization for Standardization setting, smartphone camera exposure time, USB camera LED-driving current (l), USB camera LED flux for a single LED of the given color, USB camera brightness setting, and USB exposure time are provided.

TABLE 1

| | | Smartphone camera settings | | | | USB camera settings | | | |
|---|---|---|---|---|---|---|---|---|---|
| λ (nm) | Part number | /(mA) | Flux | | ISO | Exposure time (ms) | /(mA) | Flux | | Brightness | Exposure time (ms) |
| 4000K | LXZ1-4070 | 358 | 101 | lm | 100 | 3.8 | 620 | 161 | lm | 50 | 1.6 |
| 450 | LXZ1-PR01 | 620 | 690 | mW | 100 | 0.5 | 620 | 690 | mW | 50 | 1.6 |
| 470 | LXZ1-PB01 | 620 | 46 | lm | 100 | 0.7 | 620 | 46 | lm | 50 | 1.6 |
| 500 | LXZ1-PE01 | 620 | 100 | lm | 100 | 2.6 | 620 | 100 | lm | 50 | 1.6 |
| 530 | LXZ1-PM01 | 620 | 142 | lm | 100 | 3.0 | 620 | 142 | lm | 50 | 1.6 |
| 580 | LXZ1-PL01 | 358 | 42 | lm | 100 | 5.0 | 620 | 67 | lm | 50 | 1.6 |
| 660 | LXZ1-PA01 | 620 | 420 | mW | 100 | 0.9 | 620 | 420 | mW | 50 | 1.6 |
| 810 | VSMY98145DS | 620 | 700 | mW | 2390 | 250.0 | 620 | 700 | mW | 50 | 1.6 |
| 940 | L1IZ-0940 | 358 | 403 | mW | 2300 | 180.0 | 620 | 700 | mW | 50 | 1.6 |

FIG. 3 illustrates molar extinction coefficients, ε(λ), for Hb, $HbO_2$, and melanin plotted on a log scale in the upper panel and, as mentioned earlier, the LED spectral flux probability density functions, $\phi_{e,\lambda}$, plotted on a linear scale in the lower panel.

In the example dermascope systems shown in FIGS. 1A-1E, the illumination LED PCB 120 includes three LEDs of each color (e.g., red, green, blue) soldered in a symmetrical pattern around the camera aperture to maximize uniformity without additional beam shaping optics. The backside solder mask of the PCB was removed to expose the copper and is attached to a copper heatsink with electrically insulating epoxy (DP240, 3M, St. Paul, Minnesota, USA). Numerous vias were placed on the PCB to ensure a low thermal resistance between the front and backside copper planes. The LEDs are driven with a switching boost power supply (LT3478, Linear Technology, Milpitas, California, USA) powered by two lithium-ion batteries (Orbtronic, Saint Petersburg, Florida, USA). Each LED color string can be turned on individually with a custom power level setting and/or illumination setting and synchronized with the image capture by, e.g., an Android application (also referred to as app) through, e.g., a Bluetooth-connected microcontroller (MCU, IOIO-OTG, SparkFun Electronics, Niwot, Colorado, USA). The intensity of light can be controlled, for example, by adjusting the illumination output of each of the plurality of LEDs (e.g., each of the three LEDs of the same color) individually or collectively. Example LED-driving currents, fluxes, and dermascopes' image capture settings are shown in Table 1. In addition, the smartphone camera (e.g., 170 in FIGS. 1C and 1E) or the USB camera 150 (FIG. 1A) can use the daylight white balance setting.

Figure 4C:
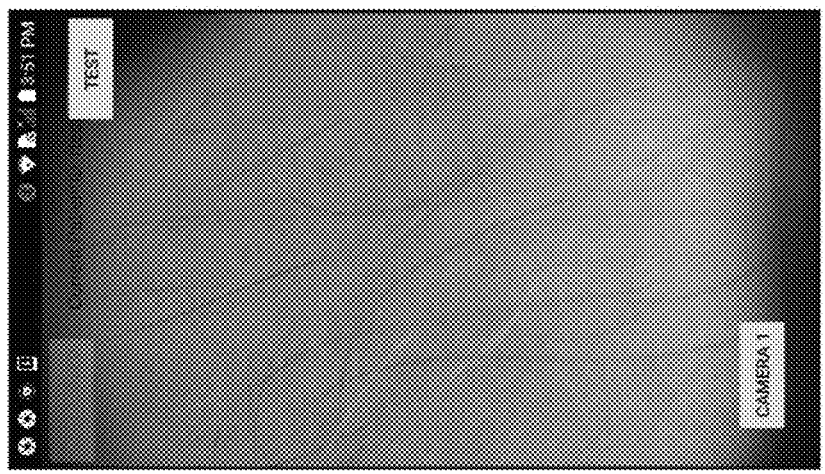
FIGS. 4B and 4C illustrate screenshots of an Android application according to an example embodiment.
Figure 4B:
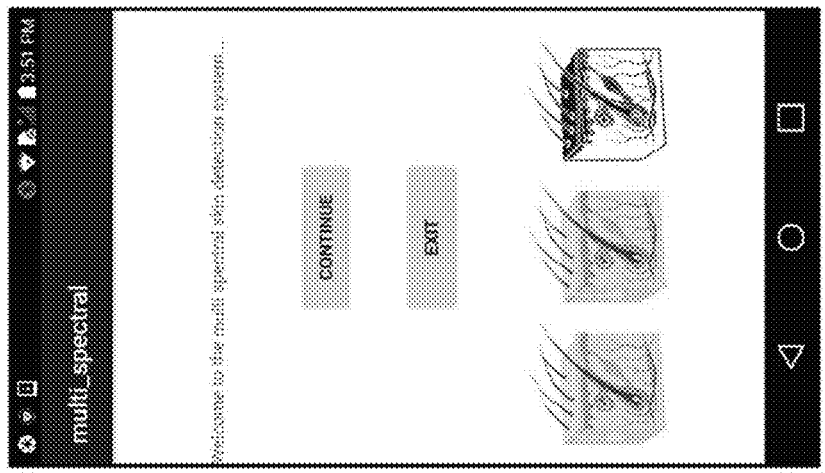
Figure 4A:
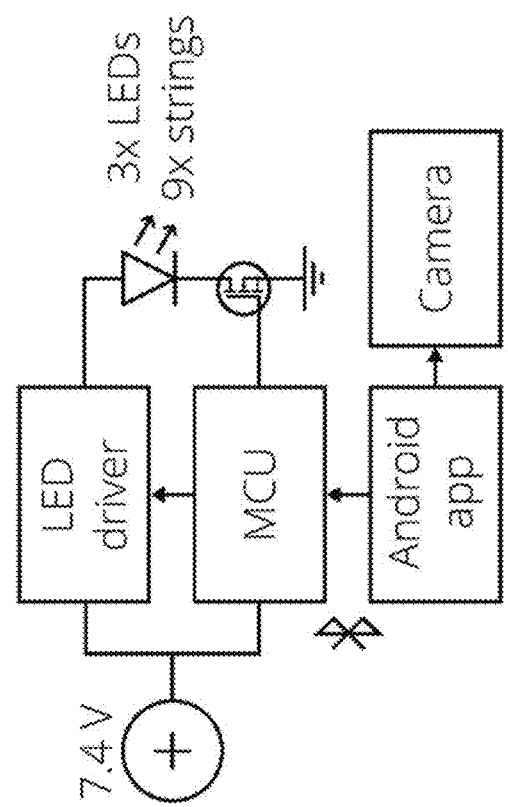
FIG. 4A illustrates an electronics block diagram of a dermascope system according to an example embodiment.

A block diagram of an example implementation of the dermascope system electronics is shown in FIG. 4. For both the USB camera and the on-board smartphone camera based dermascope systems, the Android application running, e.g., on the smartphone (e.g., smartphone 190 shown in FIG. 1E) can be configured to control the camera functions, control camera synchronization with the LED illumination, and set camera exposure time. Images captured by the camera of the dermascope system can be associated with an ID assigned to each patient, thus removing the need to store identifiable information related to the patient on the smartphone. Example screenshots of the Android app are shown in FIGS. 4A-4C.

FIG. 4A illustrates an electronics block diagram of a dermascope system according to an example embodiment. FIGS. 4B and 4C illustrate Android application screenshots. Below, operational steps, data collection methods and/or algorithms, and other operations related to the dermascope systems according to the present disclosure are described by the way of example.

Different algorithms can be used to process collected dermal images. Two example algorithms are provided in Algorithms 1 and 2 at the end of this patent document. Descriptions of the steps and related equations are provided below.

In some implementations, reference images can be collected to allow proper calibration of image parameters for later-captured images. For example, in an example implementation, images of a reflective gray card (e.g., 18% reflectivity) can be collected by a dermascope system according to the disclosed technology at one or more wavelengths to serve as both the optical density (OD) and illumination uniformity references.

For dermal image collection, a pilot study was performed on human subjects at the University of Arizona College of Medicine, Division of Dermatology to determine feasibility of each multi-spectral dermascope. This study received institutional review board approval (#1612067061). All patients provided informed written and oral consent.

The melanin content, erythema, and chromophore concentration measurements rely on conversion to the CIELAB and CIEXYZ color spaces. The imaging systems natively capture in the sRGB color space, and the images are first converted to linear RGB space:

$$C_{linear} = \begin{cases} \frac{C_{sRGB}}{12.92} & C_{sRGB} \leq 0.04045 \\ \left(\frac{C_{sRGB} + 0.055}{1 + 0.055}\right)^{2.4} & C_{sRGB} > 0.04045 \end{cases}, \quad (1)$$

where $C_{sRGB}$ is each channel of the $I_{sRGB}$ image. Images are then converted from $RGB_{linear}$ to CIEXYZ using the transformation matrix, $$\begin{bmatrix} X \\ Y \\ Z \end{bmatrix} = \begin{bmatrix} 0.4124 & 0.3576 & 0.1805 \\ 0.2126 & 0.7152 & 0.0722 \\ 0.0193 & 0.1192 & 0.9505 \end{bmatrix} \cdot \begin{bmatrix} R_{linear} \\ G_{linear} \\ B_{linear} \end{bmatrix}, \quad (2)$$

where Y is the luminance value and is used to calculate ODs from the dermis images and reference. Luminance is a measure that scales optical radiation by the response of the human visual system. Because the images will be processed by a computer, accurate color representation for a human is not required, so an additional luminance measure, $Y_{equal}$, is created using the equal sum of all three channels:

$$[Y_{equal}] = [1\,1\,1] \cdot \begin{bmatrix} R_{linear} \\ G_{linear} \\ B_{linear} \end{bmatrix}. \quad (3)$$

Using the reference images that have been converted to CIEXYZ or Yequal, reference luminance images are defined as $$I_0 = Y_{ref}, \quad (4)$$

where $Y_{ref}$ is the Y (luminance) channel of the CIEXYZ image or $Y_{equal}$. The reference grayscale image is normalized to serve as the illumination reference for the dermal images.

$$U = \frac{Y_{ref}}{\max(Y_{ref})}, \quad (5)$$

where U is now the illumination uniformity correction matrix.

The dermal CIEXYZ and Yequal images are corrected in the same way $$I_{dermal,uniformity\,corrected} = \frac{I_{dermal}}{U} \overline{U}, \quad (6)$$

where $I_{dermal}$ is the illumination uniformity corrected dermal image with constant mean luminance. Finally, OD dermal images are calculated as $$OD = -\ln\left(\frac{I}{I_0}\right). \quad (7)$$

In some example embodiments, a USB dermascope can have sections of a 18% gray photography card mounted on either side of the FOV (e.g., elements 111 and 112 in FIG. 1B). Knowing the card image should equal 50% levels of RGB, the luminance of the white-light image can be scaled using the following equation:

$$I_{dermal, luminance\ corrected} = I_{dermal, uniformity\ corrected} \frac{0.5}{Y_{gray}}. \quad (8)$$

The Beer-Lambert law can be utilized to measure the relative concentrations of Hb, oxyhemoglobin ($HbO_2$), and melanin:

$$I(\lambda) = I_0(\lambda) \exp[-c_n \varepsilon(\lambda) l(\lambda)], \quad (9)$$

where I is the resulting intensity, $I_0$ is the incident intensity, $c_n$ is the concentration of the chromophore, $\varepsilon(\lambda)$ is the molar attenuation coefficient of the chromophore at a particular wavelength, and $l(\lambda)$ is the optical path length of the light in the medium for the incident wavelength. This can be restated as OD:

$$OD = -\log\left(\frac{I(\lambda)}{I_0(\lambda)}\right) = \quad (10)$$

$$c_{Hb}\varepsilon_{Hb}(\lambda)l(\lambda) + c_{HbO_2}\varepsilon_{HbO_2}(\lambda)l(\lambda) + c_{melanin}\varepsilon_{melanin}(\lambda)l(\lambda) + c_{background},$$

where $c_{background}$ is due to residual absorption from molecules present in the epidermis and dermis.

The molar extinction coefficients for Hb and $HbO_2$ and melanin are shown in FIG. 3. Jacques's $\varepsilon_{melanin}$ was fit with an exponential curve to extend the wavelength to 1000 nm, resulting in a fit of $$\varepsilon_{melanin} = 2.2858 \cdot 10^4 \exp(-5.5028 \cdot 10^{-3} \lambda). \quad (11)$$

Optical path lengths, $l(\lambda)$, for the chromophores can be calculated from a linear fit of Anderson's data in the region of the illumination wavelengths, $$l(\lambda) = 2.62 \cdot 10^{-4} \lambda - 9.87 \cdot 10^{-2}. \quad (12)$$

where $\lambda$ is in units of nm and $l(\lambda)$ is in units of cm.

Because the LEDs are broad spectrum, we can integrate over the wavelength probability density function to calculate a total molar attenuation coefficient for each color $$\epsilon_{total} = \int \phi_{e,\lambda}(\lambda) \varepsilon(\lambda) d\lambda. \quad (13)$$

The resulting molar attenuation coefficients for the Hb, $HbO_2$, and melanin chromophores are shown in Table 2.

TABLE 2

Molar extinction coefficients calculated using Eq. (13) for each illumination wavelength compared with the molar extinction coefficients for the peak wavelength.

| | Coefficients from Eq. (13) | | | Coefficients at peak LED wavelength | | |
|---|---|---|---|---|---|---|
| Wavelength (nm) | Hb ($cm^{-1}$ $M^{-1}$) | $HbO_2$ ($cm^{-1}$ $M^{-1}$) | Melanin ($cm^{-1}$ $M^{-1}$) | Hb ($cm^{-1}$ $M^{-1}$) | $HbO_2$ ($cm^{-1}$ $M^{-1}$) | Melanin ($cm^{-1}$ $M^{-1}$) |
| 450 | 199,864 | 82,747 | 1922 | 103,292 | 62,816 | 1921 |
| 470 | 35,937 | 36,662 | 1706 | 16,156 | 33,209 | 1721 |
| 500 | 26,659 | 25,521 | 1392 | 20,862 | 20,932 | 1459 |
| 530 | 37,824 | 34,851 | 1241 | 39,036 | 39,957 | 1237 |
| 580 | 22,606 | 13,258 | 869 | 37,010 | 50,104 | 940 |
| 660 | 3380 | 352 | 611 | 3227 | 320 | 605 |
| 810 | 845 | 812 | 281 | 717 | 864 | 265 |
| 940 | 656 | 1185 | 142 | 693 | 1214 | 130 |

A system of equations is built from the multispectral datacube and the molar attenuation coefficients shown in Table 2

$$\begin{bmatrix} \varepsilon_{Hb}(\lambda_1)l(\lambda_1) & \varepsilon_{HbO_2}(\lambda_1)l(\lambda_1) & \varepsilon_{melanin}(\lambda_1)l(\lambda_1) & 1 \\ \varepsilon_{Hb}(\lambda_2)l(\lambda_2) & \varepsilon_{HbO_2}(\lambda_2)l(\lambda_2) & \varepsilon_{melanin}(\lambda_2)l(\lambda_2) & 1 \\ \varepsilon_{Hb}(\lambda_3)l(\lambda_3) & \varepsilon_{HbO_2}(\lambda_3)l(\lambda_3) & \varepsilon_{melanin}(\lambda_3)l(\lambda_3) & 1 \\ \vdots & \vdots & \vdots & \vdots \\ \varepsilon_{Hb}(\lambda_n)l(\lambda_n) & \varepsilon_{HbO_2}(\lambda_n)l(\lambda_n) & \varepsilon_{melanin}(\lambda_n)l(\lambda_n) & 1 \end{bmatrix} \begin{bmatrix} c_{Hb} \\ c_{HbO_2} \\ c_{melanin} \\ c_{background} \end{bmatrix} = \begin{bmatrix} OD(\lambda_1) \\ OD(\lambda_2) \\ OD(\lambda_3) \\ \vdots \\ OD(\lambda_n) \end{bmatrix}. \quad (14)$$

and the system is solved by linear algebra least-squares techniques where $OD(\lambda_n)$ are calculated OD matrices for each illumination wavelength.

The ability of the dermascopes according to the present disclosure to properly measure relative chromophore concentrations was validated using a finger occlusion test. Images were taken with both dermascopes illustrated in FIGS. 1A-1E and the chromophores were mapped preocclusion, after 2 min of occlusion, postocclusion, and 5 min after ending the occlusion.

To measure melanin content and erythema, the white-light image can be converted to the CIELAB color space using lightness (L*) as a measure of relative melanin content and the direction of red color stimuli (a*) as a measure of redness, with more positive values indicating higher levels of erythema. Before converting to CIELAB, normalization constants can be calculated from the white-LED spectral content. Using the color matching functions, $\bar{x}(\lambda), \bar{y}(\lambda), \bar{z}(\lambda)$ (FIG. 5), X, Y, and Z can be calculated as.

$$X = \int_{380\ nm}^{780\ nm} \bar{x}(\lambda) \phi_{e,\lambda} d\lambda; Y = \int_{380\ nm}^{780\ nm} \bar{y}(\lambda) \phi_{e,\lambda} d\lambda; Z = \int_{380\ nm}^{780\ nm} \bar{z}(\lambda) \phi_{e,\lambda} d\lambda, \quad (15)$$

where $\phi_{e,\lambda}$ is the relative spectral flux of the white-LED source as shown in FIG. 3. The normalization constants $X_n$, $Y_n$, and $Z_n$ can be calculated as $$X_n = \frac{X}{Y}; Y_n = \frac{Y}{Y}; Z_n \frac{Z}{Y}. \quad (16)$$

The image can be then converted to CIELAB by $$L^* 116 f\left(\frac{Y}{Y_n}\right) - 16, a^* = 500\left[f\left(\frac{X}{X_n}\right) - f\left(\frac{Y}{Y_n}\right)\right], \quad (17)$$

$$b^* = 200\left[f\left(\frac{Y}{Y_n}\right) - f\left(\frac{Z}{Z_n}\right)\right],$$

where $$f(x) = \begin{cases} x^{1/3} & x > (24/116)^3 \\ (841/108)x + 16/116 & x \leq (24/116)^3 \end{cases}. \quad (18)$$

Figure 5:
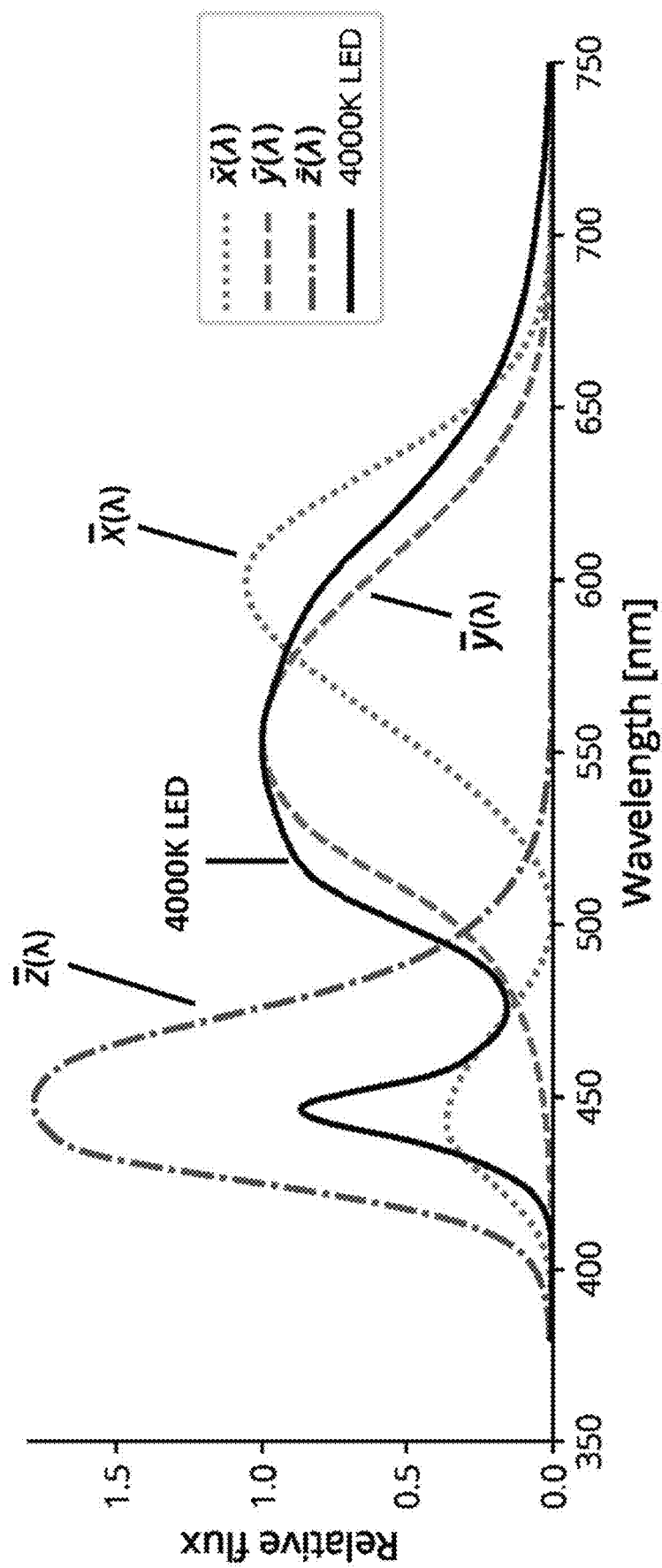
FIG. 5 illustrates example color matching curves which can be used to determine normalization constants to convert to CIELAB color space along with the 4000 K white-LED spectrum.

FIG. 5 illustrates color matching curves used to determine normalization constants to convert to CIELAB along with the 4000 K white-LED spectrum.

In addition to the white-light image measures, melanin and erythema measures can be constructed from the color-OD images. Melanin content can be calculated as $$\text{Melanin} = OD_{660} - OD_{940}. \quad (19)$$

As shown in Table 2, these two wavelengths maximize the difference in melanin absorption and minimize the effect of Hb and $HbO_2$ absorption.

Erythema, due to increased blood content, results in increased blue light absorption but little change in red light absorption as shown in Table 2. Therefore, an erythema index can be constructed as $$\text{Erythema} = OD_{470} - OD_{660}. \quad (20)$$

The linearity of the camera responses was measured by adjusting the exposure time in the case of the smartphone-camera-based dermascope and image brightness in the case of the USB-camera-based dermascope, capturing images of the matte 18% gray photography card with each LED color, and measuring the image luminance mean at each wavelength.

Performance of the imaging system's cutoff frequency and FOV was validated with a 1951 United States Air Force (USAF) resolution test chart, and the modulation transfer function (MTF) was measured using the slanted-edge method.

Illumination uniformity was measured by illuminating the matte 18% gray photography card with each LED color and imaging the surface of the card with the dermascope. The uniformity is quantified using the coefficient of variation, ($c_v$), on normalized data $$\text{Uniformity} = 1 - c_v = 1 - \frac{\sigma}{\bar{x}}, \quad (21)$$

where $\bar{x}$ is the mean of the pixels in the image and $\sigma$ is the standard deviation of the pixel values.

RGB, chromophore, melanin, and erythema measures for cases of junctional nevus (JN) and squamous cell carcinoma (SCC) are shown in FIGS. 6A-6F and 7A-7F, respectively. Each case was captured with both the USB camera dermascope and the smartphone camera dermascope.

Figure 8:
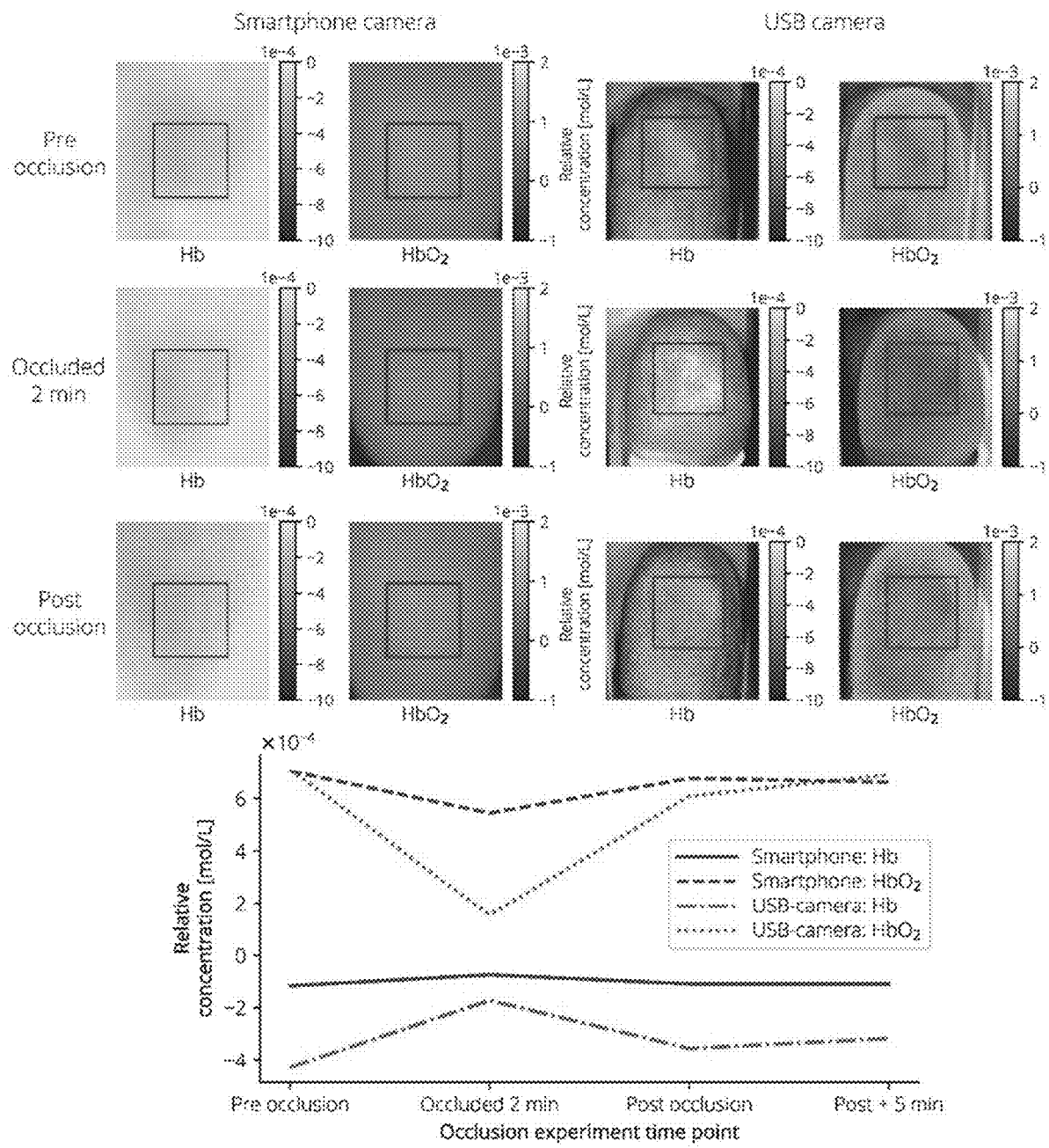
FIG. 8 illustrates chromophore maps for an example embodiment of a USB camera dermascope and an example embodiment of a smartphone camera dermascope at certain time points during an occlusion test.

The chromophore maps for both dermascopes at the chosen time points for the occlusion test are shown in FIG. 8.

Figure 9:
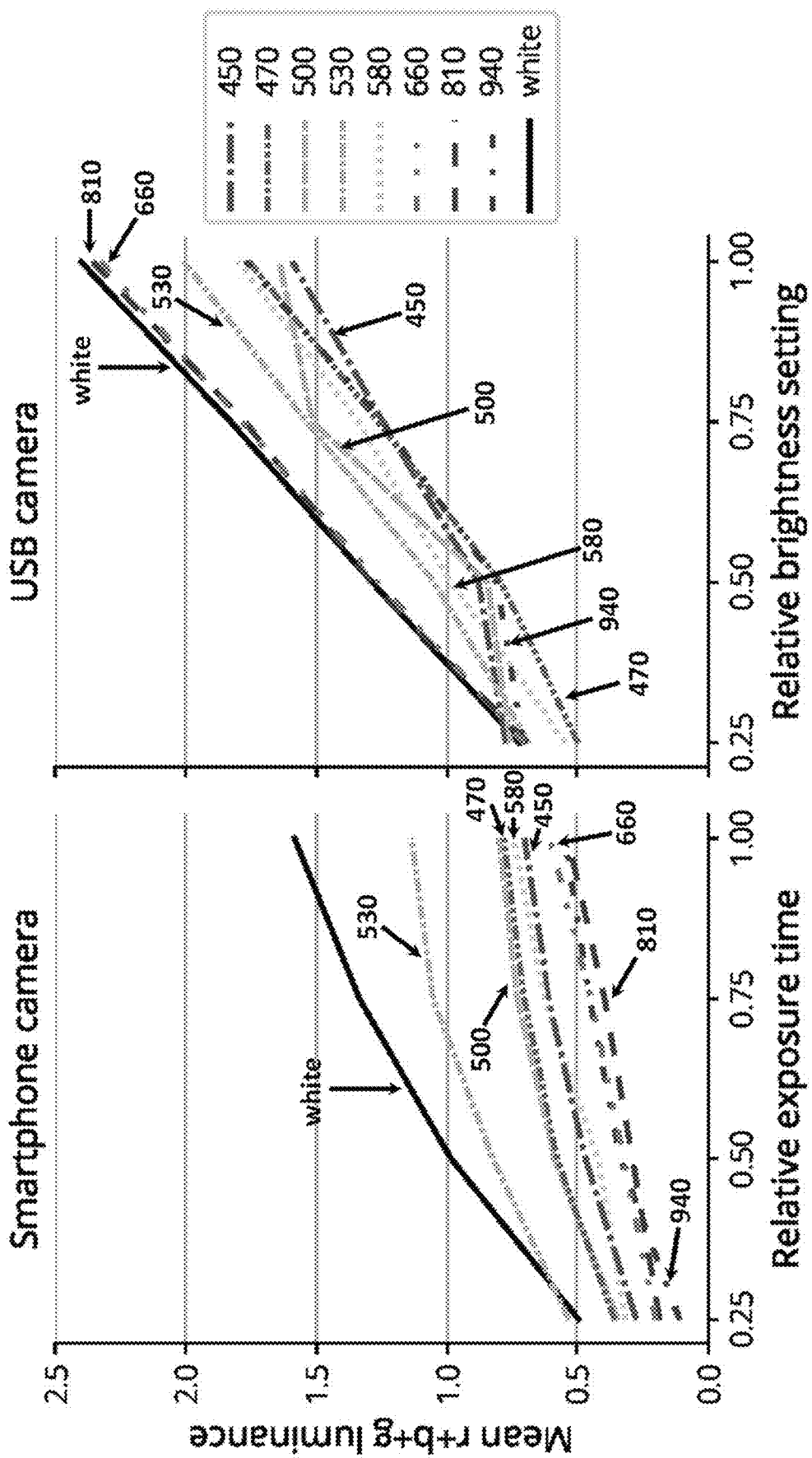
FIG. 9 shows changes in a mean of a sum of the red, green, and blue image channels over varying exposure times for an example embodiment of a smartphone camera based dermascope and over brightness settings for an example embodiment of a USB camera based dermascope.

FIG. 9 shows the changes in the mean of the sum of the red, green, and blue image channels over varying exposure times for the smartphone camera based dermascope and over brightness settings for the USB camera based dermascope.

FIGS. 10A-10F show full-field and zoomed 1951 USAF resolution test chart images after cropping along with MTF data measured using the slanted-edge test for both dermascopes.

Figure 11:
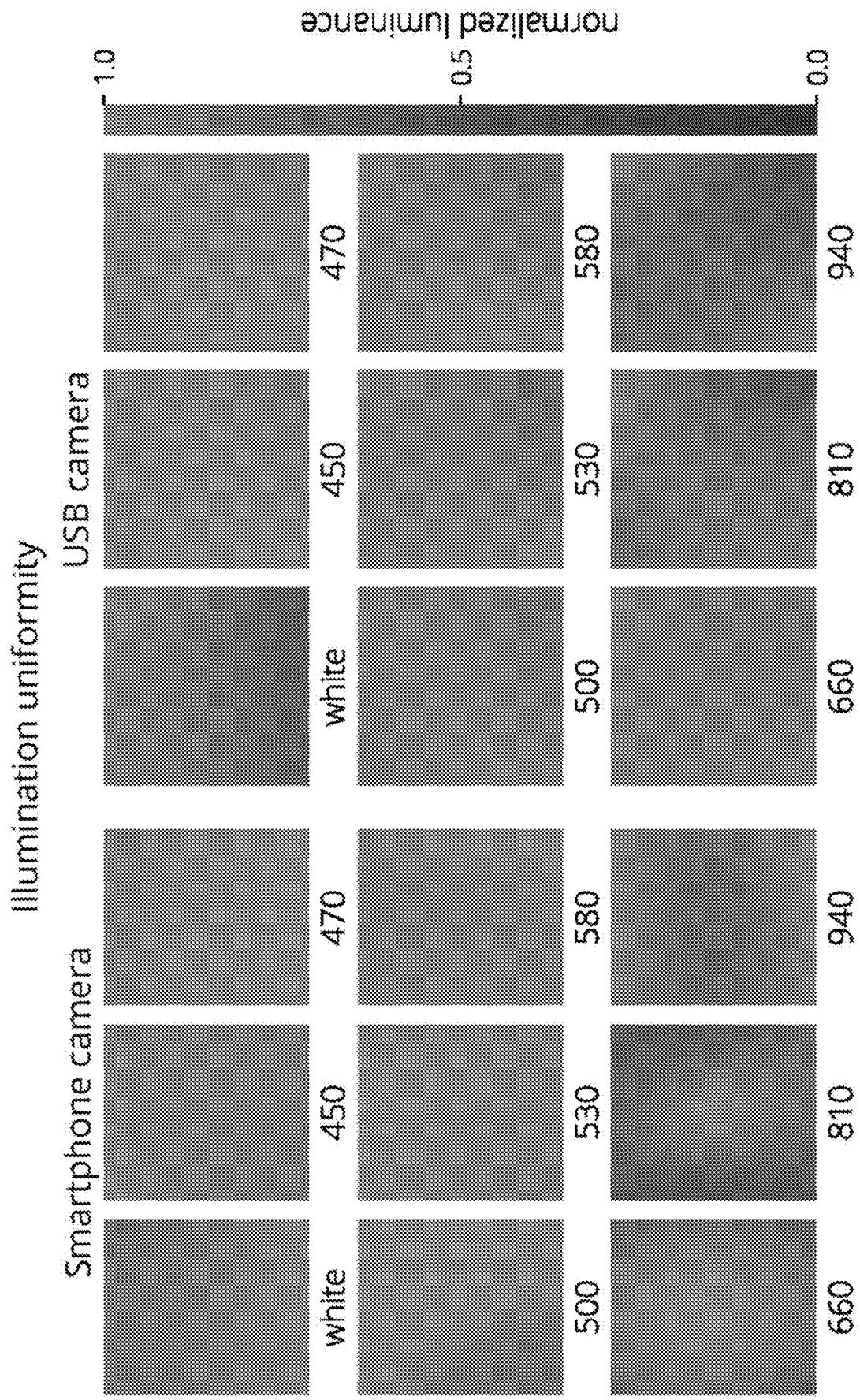
FIG. 11 shows example maps of illumination uniformities for a smartphone camera based dermascope and a USB camera based dermascope according to the disclosed technology.

Maps of the illumination uniformities of both systems are shown in FIG. 11, and the coefficients of variations are given in Table 3.

The CIEXYZ normalization constants calculated from the white-LED spectrum for the two dermascopes (a smartphone camera based dermascope and a USB camera based dermascope according to the present disclosure) are shown in Table 4.

Figures 6D, 6E, 6F:
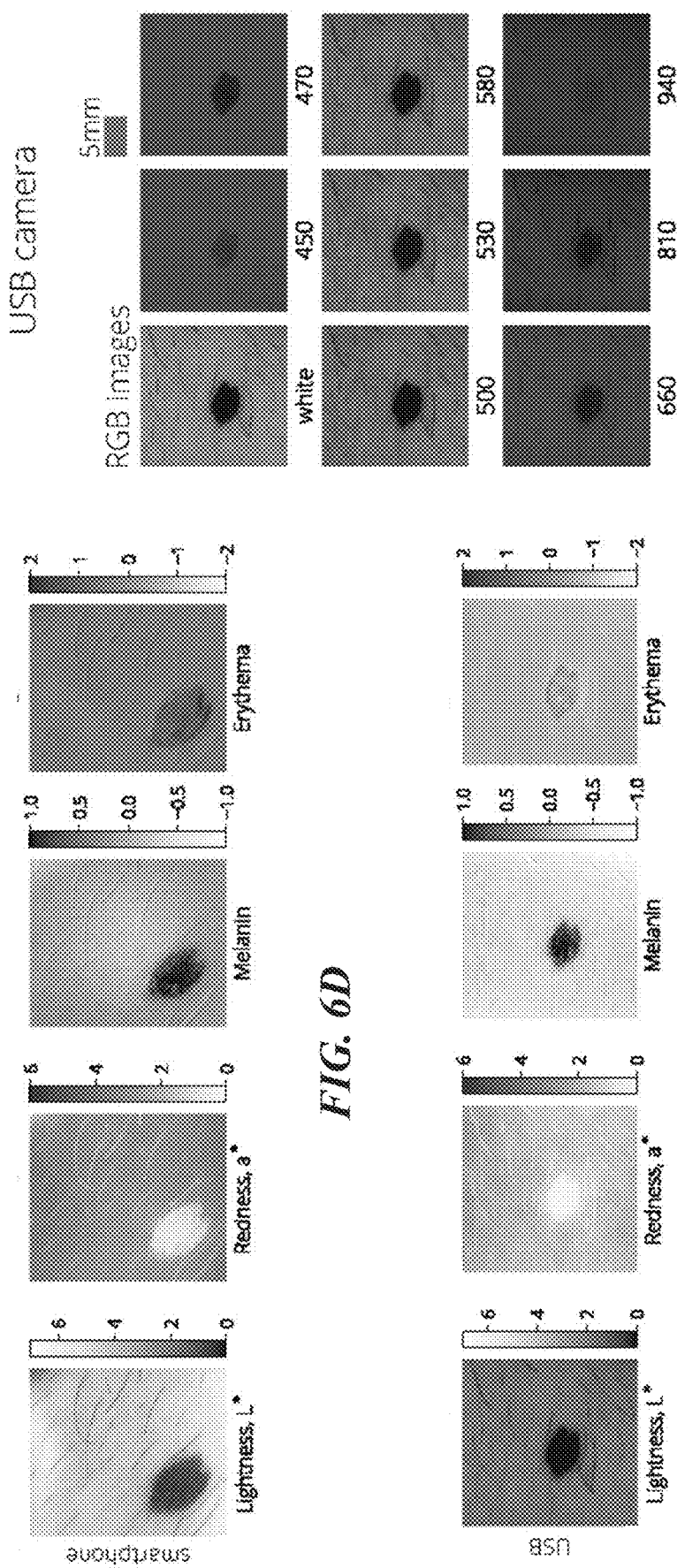

FIGS. 6A-6F illustrate the same JN imaged by both the smartphone and USB dermascopes. For the smartphone dermascope, FIG. 6A illustrates the RGB images after illumination uniformity correction, FIG. 6B illustrates the relative chromophore concentrations, and FIG. 6D illustrates lightness as measured by L*, redness as measured by a*, melanin calculated from Eq. (19), and erythema calculated from Eq. (20). The same measures are shown for the USB dermascope in FIGS. 6F, 6C, and 6E, respectively. A 5-mm scale bar is provided for both the smartphone-camera images and the USB camera images above the RGB image grids.

FIGS. 7A-7F illustrate the same SCC imaged by both the smartphone and USB dermascopes. For the smartphone dermascope, FIG. 7A illustrates the RGB images after illumination uniformity correction, FIG. 7B illustrates the relative chromophore concentrations, and FIG. 7D illustrates lightness as measured by L*, redness as measured by a*, melanin calculated from Eq. (19), and erythema calculated from Eq. (20). The same measures are shown for the USB dermascope in FIGS. 7F, 7C, and 7E, respectively. A 5-mm scale bar is provided for both the smartphone-camera images and the USB camera images above the RGB image grids.

The distribution of polarized multispectral dermascopes according to the disclosed technology which are based on smartphone platforms and low-cost color LEDs to PCPs (and eventually to consumers) has the potential to democratize dermal chromophore and melanoma mapping along with erythema monitoring, improving quantitative monitoring of lesions and increasing early detection of skin cancers.

These smartphone based platforms demonstrate a number of advantages compared with previous systems targeting chromophore mapping and skin cancer screening. The smartphone based dermascope platform according to the disclosed technology is a compact, low-cost, portable, easy-to-use system with native image capture and processing capabilities, which removes the need for expensive, clinical-grade imaging systems. The platform is flexible enough to use either the camera embedded in a mobile device (e.g., a smartphone or a tablet) for imaging or a separate USB camera connected to the mobile device, depending on the desired ergonomics of the user. Both system implementations can still use the built-in smartphone camera for wide-field, white-light, and dermal imaging (e.g., the annulus 110 in FIG. 1C can be removed). Additionally, the smartphone camera can be used for large area image capture either using the smartphone-camera-based dermascope with the imaging annulus removed or using the USB camera's host smartphone.

FIG. 8 illustrates finger occlusion test results for the smartphone camera and USB camera at preocclusion, after occlusion for 2 min, and postocclusion. The bottom plot in FIG. 8 provides the mean relative concentration for Hb and $HbO_2$ inside the rectangle showing a dip in $HbO_2$ and increase in Hb after occlusion.

FIG. 9 illustrates mean of the sum of the red, green, and blue channels over changing exposure times for the smartphone camera based dermascope and changing brightness settings for the USB camera based dermascope.

Figure 10A:
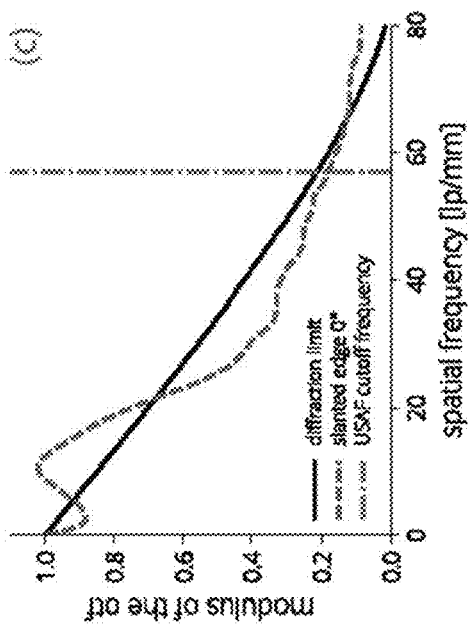
FIGS. 10A-10F show full-field and zoomed 1951 USAF resolution test chart images after cropping along with modulation transfer function (MTF) data measured using the slanted-edge test for a smartphone camera based dermascope and a USB camera based dermascope according to the present disclosure.
Figure 10B:
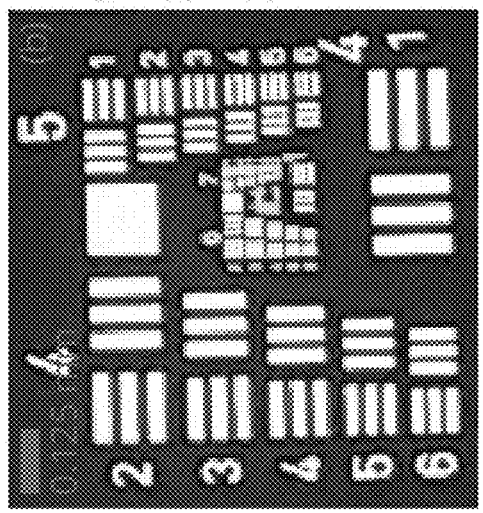
Figure 10C:
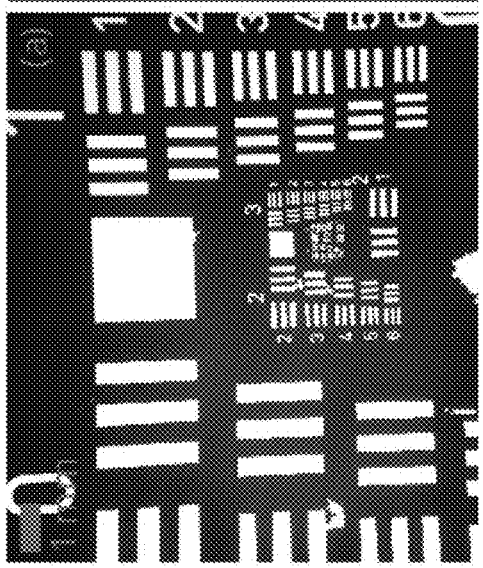
Figure 10D:
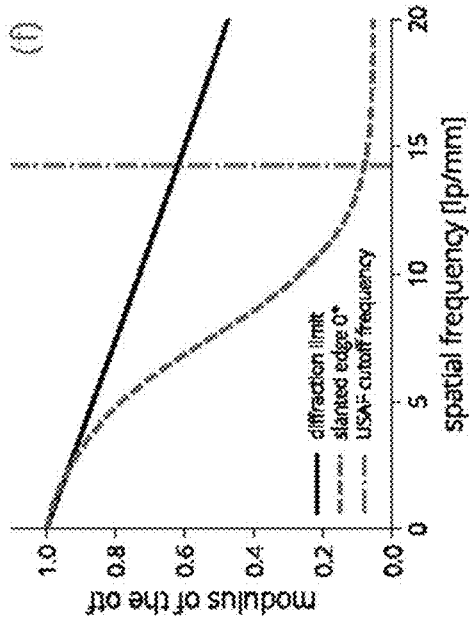
Figure 10E:
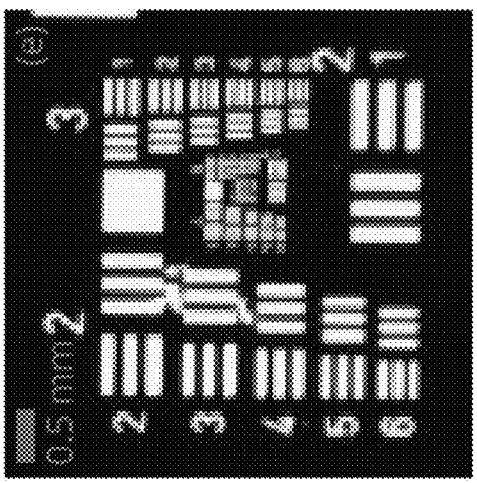
Figure 10F:
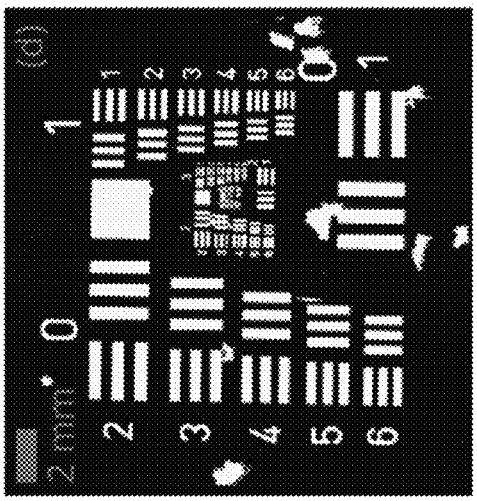

FIGS. 10A-10C illustrate smartphone camera and FIGS. 10D-10F illustrate USB camera results of 1951 USAF resolution test chart imaging along with measured MTFs from a slanted-edge test. The smartphone camera's measured MTF matches the USAF cutoff frequency of group 5 to 6 (57 lp/mm). The USB camera's measured MTF matches the USAF cutoff frequency of group 3 to 6 (14.25 lp/mm).

FIG. 11 illustrates normalized luminance maps showing illumination uniformity of each device and each illumination wavelength corresponding to U in Eq. (5)

The use of low-cost, compact, high-power, high-efficacy, surface mount LEDs improves on the costs and complexities associated with laser-based, interference-filter-based, and spectrometer-based dermascope systems. While these systems likely allow for better discrimination due to their narrow-bandwidth sources or detection schemes, the costs involved (with the possible exception of the laser-based systems) are prohibitive. High-reliability LEDs are available in myriad wavelengths to probe various points along the chromophore molar attenuation curves (FIG. 3) and can be powered with simple driving circuits. Surface-mount packages remove the bulk of transistor outline can packages (or larger packages) necessary for edge-emitting lasers, and the broad wavelength selection is wider than that of surface mount laser packages such as vertical-cavity surface-emitting lasers. The cost of LED sources compared with laser sources or interference filters allows for the use of multiple wavelengths in a single system while keeping bill of materials (BOM) costs low.

TABLE 3

LED illumination uniformity according to Eq. (21).

| Wavelength | Smartphone camera | USB camera |
|---|---|---|
| White | 0.954 | 0.880 |
| 450 | 0.974 | 0.980 |
| 470 | 0.982 | 0.977 |
| 500 | 0.935 | 0.969 |
| 530 | 0.977 | 0.955 |
| 580 | 0.980 | 0.949 |
| 660 | 0.916 | 0.972 |
| 810 | 0.852 | 0.900 |
| 940 | 0.907 | 0.870 |

TABLE 4

Measured CIEXYZ normalization constants for both dermascopes.

|  | Smartphone camera | USB camera |
|---|---|---|
| $X_n$ | 82.873 | 82.846 |
| $Y_n$ | 100 | 100 |
| $Z_n$ | 34.567 | 48.757 |

In clinical testing, both systems (a smartphone camera based dermascope and a USB camera based dermascope according to the present disclosure) were able to capture full image datasets and return similar results of relative chromophore concentrations across multiple dermal lesions except for Hb in the JN case, as shown in FIGS. 6A-6F. The deviation could be explained by the difference in IR imaging performance between the two dermascopes.

In addition, relative melanin content and erythema as measured through the CIELAB white-light images and OD color images agreed between the systems and are reasonable based on visual examination. The USB camera and smartphone camera have differing levels of luminance in their white-light images as seen in FIGS. 6A-6F and 7A-7F, leading to a difference in baseline lightness and redness values, where the higher luminance smartphone images show higher overall L* and a* values. However, as seen in FIGS. 6A-6F, the relative changes are similar, where $\Delta L^* \approx 3$ between the nevus and surrounding skin and $\Delta a^* \approx 3$ between the nevus and surrounding skin.

The occlusion test (FIG. 8) provided directionally correct results for both dermascopes, although the magnitudes of change in chromophore concentration were dissimilar between dermascopes. Again, this deviation could be explained by the difference in IR imaging performance between the two dermascopes.

Once a large dataset reflecting multiple types of skin lesions in addition to a wide range of baseline melanin levels in patients is collected along with biopsy and diagnosis results, classification algorithms can be built using machine learning, principal components analysis, or similar tools. The statistics of the large dataset and the classifier can then be used to predict the relationships between chromophores, lesion type, and diagnosis. In our two datasets, high-melanin concentrations were present for the JN case but not for the SCC case. The classifier can help to determine if this relationship is true more generally or how this might change in patients with high baseline levels of melanin. Likewise, while the Hb and $HbO_2$ levels were similar in our two datasets, a larger dataset might reveal that cancerous activity increases blood flow, increasing both Hb and $HbO_2$ and possibly the ratios between them. The classifier could use additional features and relationships in the images. For example, by Eq. (12), the optical path length increases as the wavelength increases, increasing the probe depth. Detecting lesion shape changes over depth through edge detection or similar means could provide another layer of information. Indications of these changes are apparent in both the JN and SCC cases as both have changing edges as the wavelength changes. Likewise, the classifier could potentially use additional measures such as blood contrasts and oxygenation percentages.

Both cameras produced approximately linear responses when changing exposure time in the case of the smartphone camera dermascope and brightness in the case of the USB camera dermascope, providing confidence in the ability of the systems to have a linear response to intensity changes from illumination absorption.

For the smartphone dermascope, the measured MTF performance matched both the predicted diffraction-limited performance and the cutoff frequency measured with the USAF target where group 5 to 6 (57 lp/mm) is resolvable. The root mean square error (RMSE) between the measured MTF and predicted diffraction-limited performance was RMSE=0.97. The USB dermascope's measured MTF performance did not match the predicted diffraction-limited performance (RMSE=0.384); however, full specifications of the imaging lens are not provided by the manufacturer, precluding a more accurate estimation of the true diffraction-limited performance. The lens' NA was estimated to be 0.004 based on the slanted-edge measurement. The measured MTF cutoff frequency matched the USAF target measurement where group 3 to 6 (14.25 lp/mm) was resolvable. As shown in the dermal images, both dermascopes demonstrated sufficient image quality for most reasonably sized lesions, with the ability to resolve features as small as 17 μm for the smartphone dermascope and 70 μm for the USB dermascope.

Illumination uniformity was greater than 85% for all wavelengths with both dermascopes and was easily corrected in the image processing algorithms.

In some embodiments, further improvements can be made by incorporating color-to-color spatial image registration to reduce image blur at the border markings. Increasing capture speed also reduces the likelihood for image blur between images, easing the need for color-to-color image registration while faster image capture would also increase patient comfort. In systems where image capture speed is not able to be increased, having added markings would likely improve registration because they provide high contrast, well-defined features to extract.

In some embodiments where the portable electronic device has two (or in general more than one) rear cameras, the multiple cameras can be used to provide depth imaging and enable stereoscopic 3D imaging to provide a topography of the skin lesion. Alternatively, each of the multiple cameras could provide different FOVs or different NAs for imaging flexibility.

In some embodiments, additional illumination optics, such as diffusers, are used to increase illumination uniformity. The LED board was originally designed to take advantage of the dual cameras of the LG G5, but reducing the center aperture of the LED board can increase illumination uniformity and reduce system size. LED wavelengths can also be tailored to the task or expanded into UV wavelengths to probe potential autofluorescence signatures.

In an example use case, the smartphone-based dermascopes for dermal lesion screening and erythema monitoring using PMSI and PWLI described herein can augment the capabilities of PCPs, with the potential for earlier detection of melanoma and NMSC along with quantitative monitoring of erythema. The combination of LED sources, 3D-printing, and smartphone-based imaging enables the creation of low-cost (a high-volume BOM cost of <$40 excluding the smartphone should be easily achievable), feature-rich, easy-to-use medical imaging devices using either a smartphone camera or a USB camera.

Figure 12:
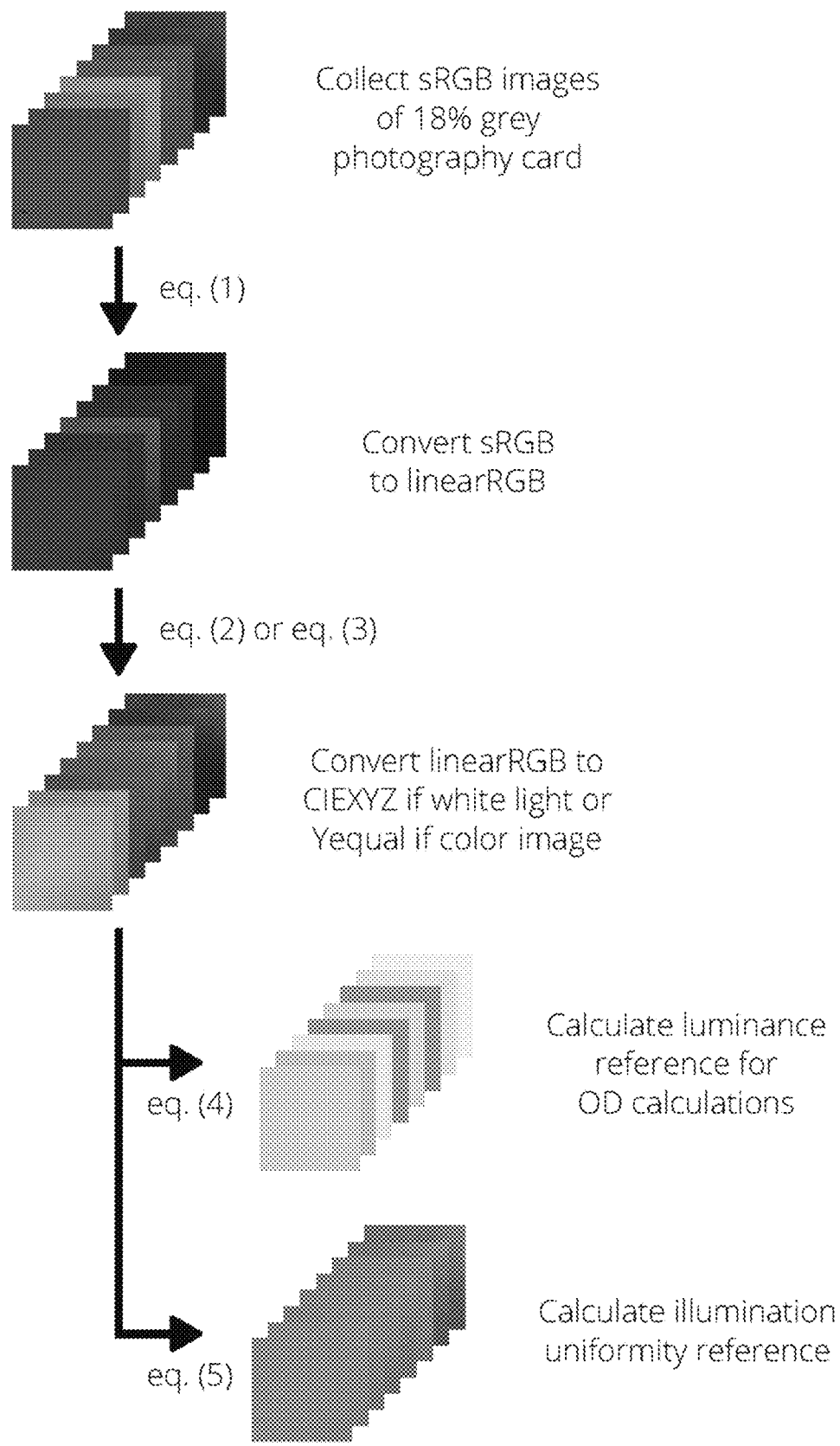
FIG. 12 show a flow diagram of an example embodiment of a method of processing reference images according to an example embodiment.
Figure 13:
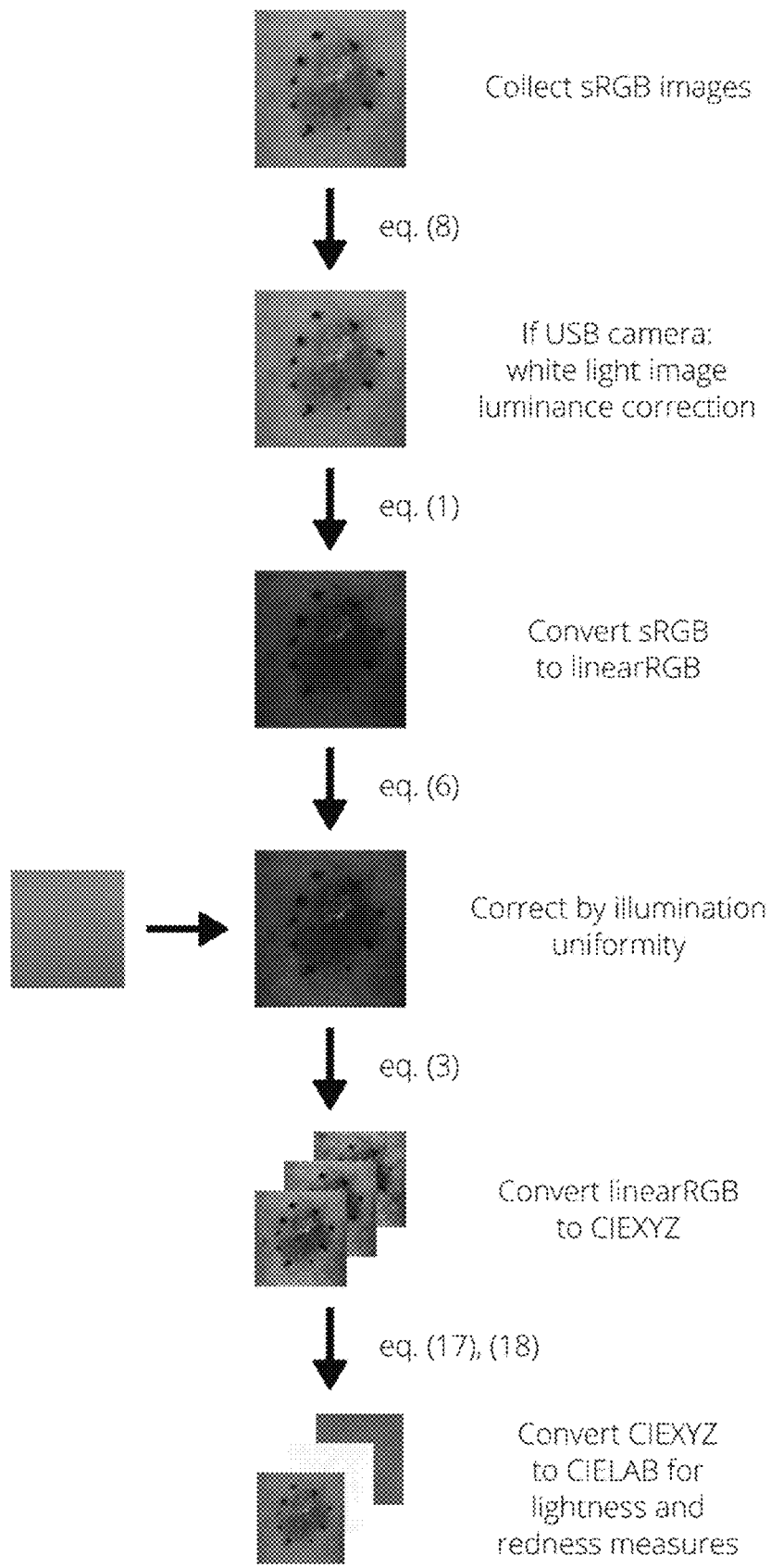
FIG. 13 show a flow diagram of an example embodiment of a method of processing white-light images according to another example embodiment.
Figure 14:
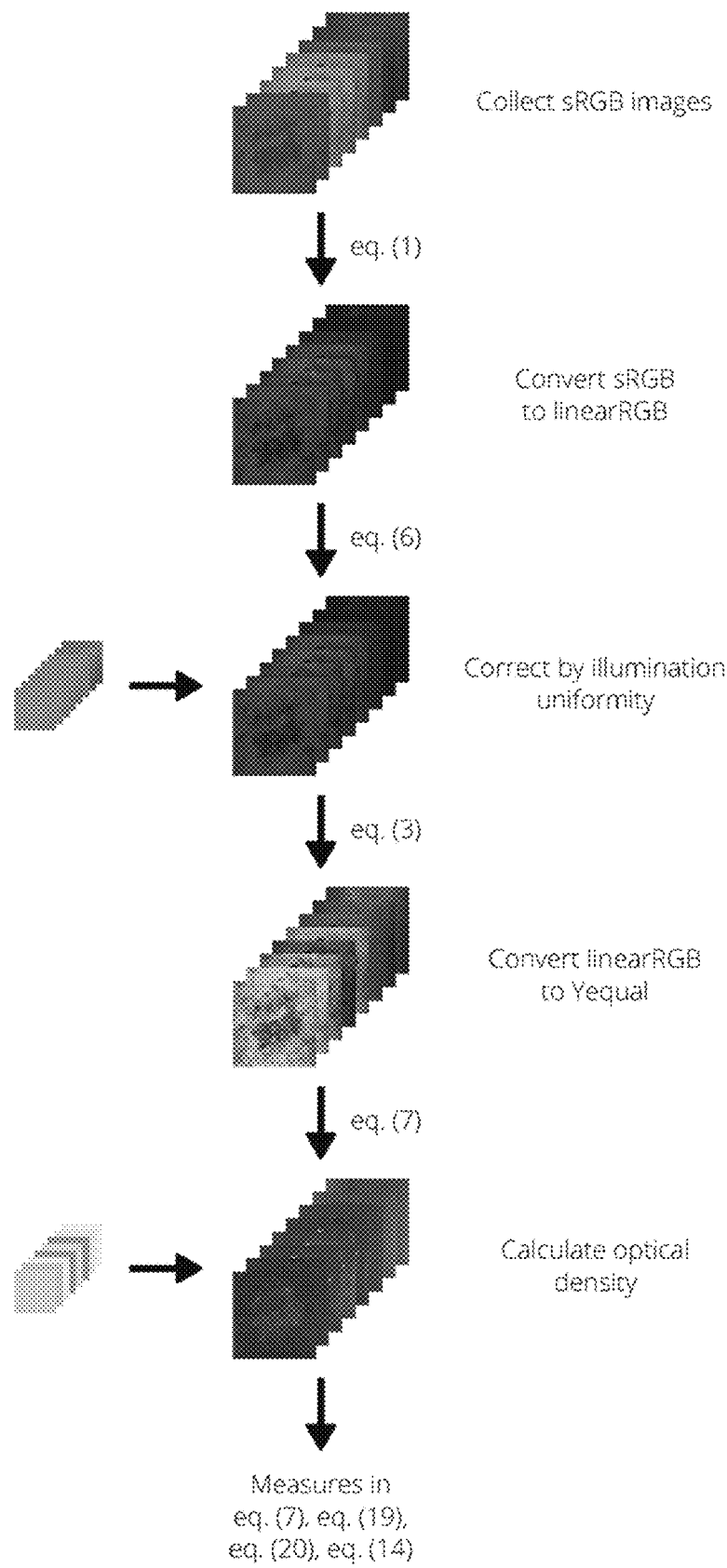
FIG. 14 show a flow diagram of an example embodiment of a method of processing multispectral images according to an example embodiment.

FIGS. 12-14 provide flowcharts to help visualize the processing algorithms for the reference, white-light images, and color images provided in Algorithms 1 and 2.

FIG. 12 show a flow diagram of an example embodiment of a method of processing reference images according to Algorithm 1.

FIG. 13 show a flow diagram of an example embodiment of a method of processing white-light images according to Algorithm 2.

FIG. 14 show a flow diagram of an example embodiment of a method of processing multispectral images according to Algorithm 2.

Figure 15:
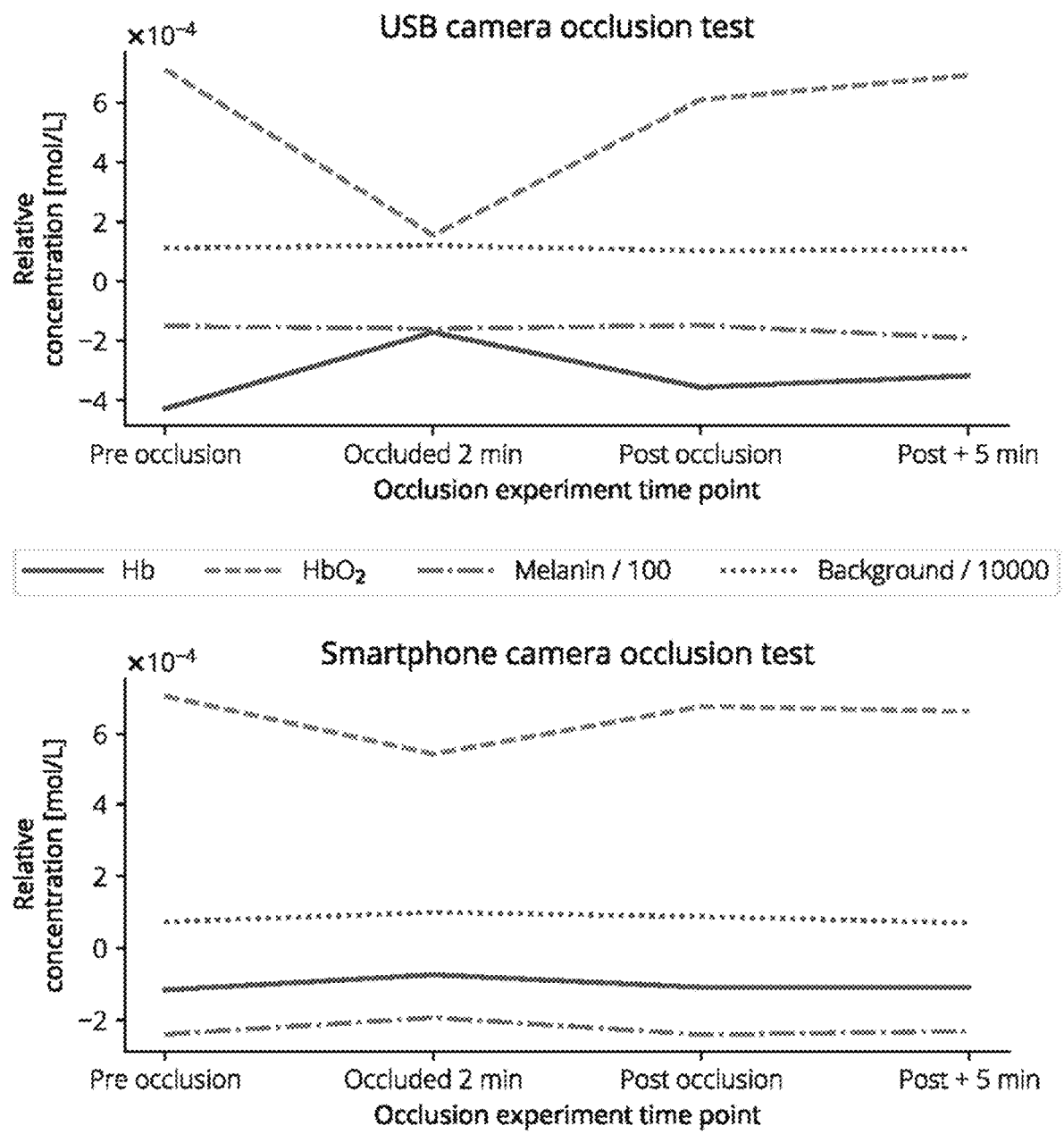
FIG. 15 illustrates example finger occlusion test results for a smartphone camera a USB camera.

While the Hb and $HbO_2$ chromophore levels should change during the finger occlusion test as shown in FIG. 8, the melanin and background measures should remain constant. FIG. 15 shows the additional measures during the occlusion test. Here, the melanin measure has been divided by 100 and the background measure divided by 10,000 for easier comparison of changes between measures. Here, the USB camera's melanin and background measurements are more stable over the time points compared with the smartphone camera.

FIG. 15 illustrates finger occlusion test results for the smartphone camera and USB camera at pre-occlusion, after occlusion for 2 min, and postocclusion for Hb, $HbO_2$, melanin, and background measures resulting from Eq. (14). Here, the melanin measure has been divided by 100 and the background measure divided by 10,000 for easier comparison with the changes in Hb and $HbO_2$.

Figure 16:
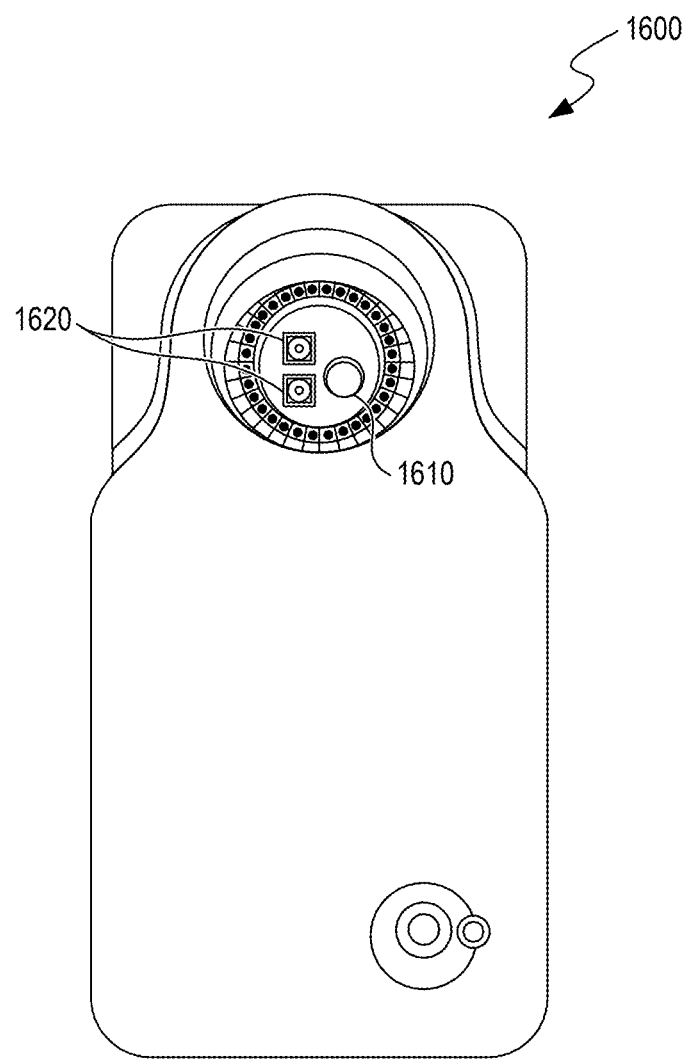
FIG. 16 shows a dermascope according to an example embodiment.

FIG. 16 shows a dermascope 1600 according to an example embodiment. The dermascope illustrated in FIG. 16 includes internal mobile imaging sensor(s) 1610 and external imaging sensor(s) 1620 to capture images over the same region of the skin. Such configuration enables, among other features and benefits, obtaining different information regarding skin properties based on the captured images. For example, with more than one sensor imaging the same region sequentially, the images with different skin properties can be correlated accurately for further analysis. The configuration of FIG. 16 also overcomes the limitations of the internal mobile imaging sensor—i.e., typically a color sensor having a short pass filter to block the light beyond 700 nm—by providing an external imaging sensor(s) that can be monochromatic and/or color sensors but, e.g., without the short pass filter. With different spectral filters, such as a long pass filter, a short pass filter, and a band pass filter, the monochromatic sensor can capture additional skin properties, such as autofluorescence. By orienting a polarizer in front of each sensor at different angles relative to the polarizer in front of the LEDs, more information on the skin polarization properties can be obtained as well. With two or more external sensors, 3D skin tomography can also be obtained.

Figure 17:
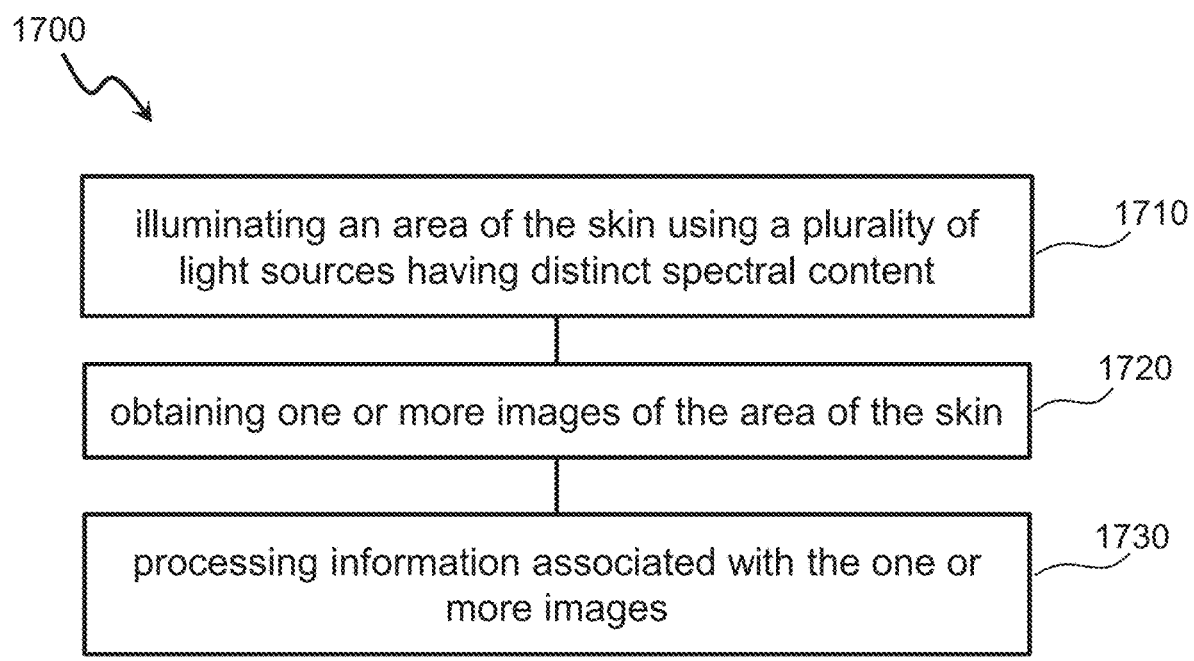
FIG. 17 shows a flow diagram of an example embodiment of a method according to the disclosed technology.

FIG. 17 shows a flow diagram of an example embodiment of a method 1700 according to the disclosed technology. The method 1700 includes a process 1710 of illuminating an area of the skin using a plurality of light sources having distinct spectral content to provide illumination in a plurality of distinct wavelengths or range of wavelengths where deoxyhemoglobin, oxyhemoglobin, or melanin exhibit differing optical characteristics. The method 1700 further includes a process 1720 of obtaining one or more images of the area of the skin. The method 1700 also includes a process 1730 of processing information associated with the one or more images to obtain a level of at least one chromophore in the skin.

Figure 18:
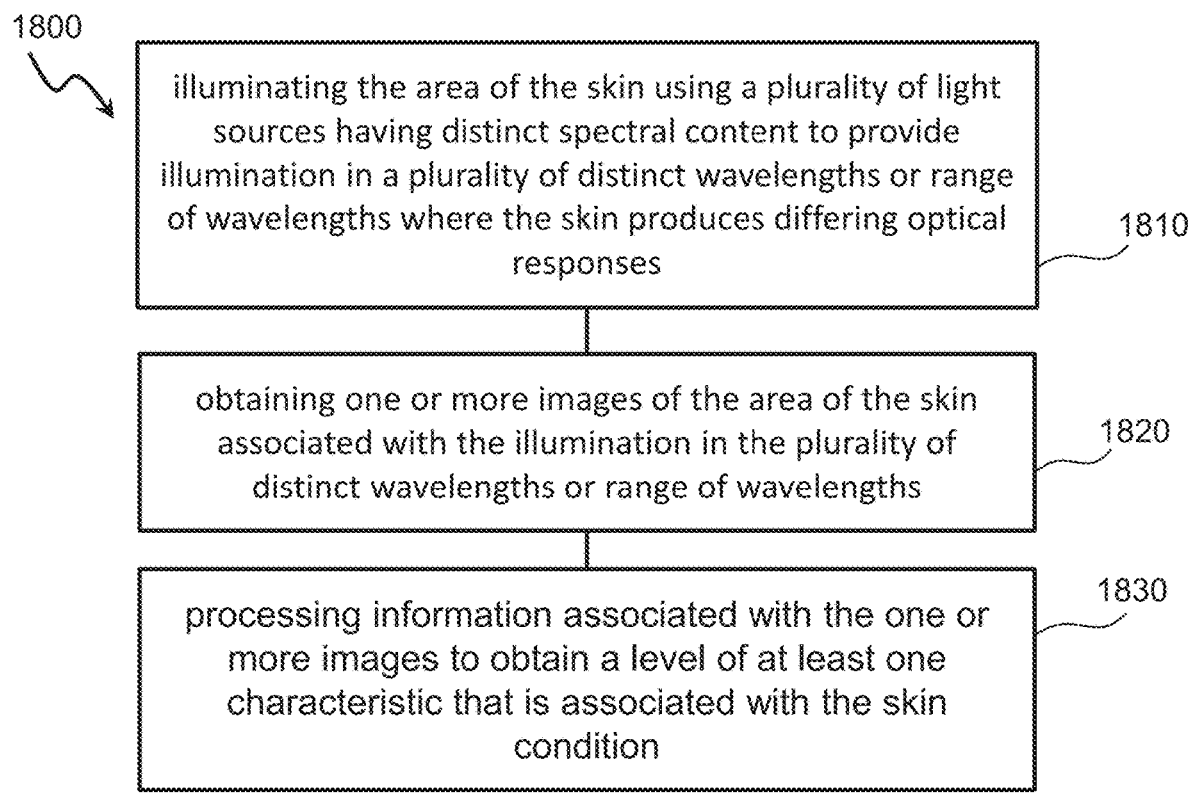
FIG. 18 shows a set of operations for imaging an area of a skin facilitate a determination of a skin condition in accordance with an example embodiment.

FIG. 18 shows a set of operations 1800 for imaging an area of a skin facilitate a determination of a skin condition in accordance with an example embodiment. At 1810, an area of a skin is illuminated using a plurality of light sources having distinct spectral content to provide illumination in a plurality of distinct wavelengths or range of wavelengths where the skin produces differing optical responses. At 1820, one or more images of the area of the skin associated with the illumination in the plurality of distinct wavelengths or range of wavelengths is obtained. At 1830, information associated with the one or more images is processed to obtain a level of at least one characteristic that is associated with the skin condition. In one example embodiment, the differing optical responses include responses that are based on differing optical characteristics of deoxyhemoglobin, oxyhemoglobin, or melanin in response to illumination in the plurality of distinct wavelengths or range of wavelengths, and the processing produces the level of at least one chromophore in the skin.

An aspect of the disclosed embodiments relates to a dermascope for imaging an area of a skin, comprising: a plurality of light sources having different spectral contents and configured to illuminate the area of the skin; at least one imaging sensor configured to collect images of the area of the skin; a processor and a memory comprising instructions stored thereon, wherein the instructions upon execution by the processor, cause the processor to: control illumination provided by the plurality of light sources to the area of the skin, and process information associated with the images produced from reflected light from the area of the skin to enable detection of a level of one or more chromophores in the skin, wherein illumination from the plurality of light sources is controlled to provide illumination in a plurality of distinct wavelengths or range of wavelengths where the one or more chromophores exhibit differing optical characteristics.

In some example embodiments of the dermascope, the processor is configured to determine an optical density value associated with two or more of the plurality of distinct wavelength. According to some example embodiments, the processor is configured to determined one or both erythema or melanin based on the determined optical density values. In an example embodiment, the plurality of distinct wavelengths or range of wavelengths is selected to include two or more wavelengths at which at least two chromophores exhibit differing extinction coefficients. In another example embodiment, at a first of the two or more wavelengths, a first of the at least two chromophores has a higher molar extinction coefficient than a second of the at least two chromophores, at a second of the two or more wavelengths, the first of the at least two chromophores has a lower molar extinction coefficient than the second of the at least two chromophores. In some example embodiments, at a third wavelength, the first and the second of the at least two chromophores have substantially similar molar extinction coefficients.

According to some example embodiments, the two or more wavelengths at which the at least two chromophores exhibit differing extinction coefficients correspond to two or more wavelengths at which that at least two chromophores exhibit two or more largest differences in their extinction coefficients. In some example embodiments, the chromophores include one or more of deoxyhemoglobin, oxyhemoglobin, or melanin. In an example embodiment, the plurality of light sources includes a white light source. In some example embodiments, the dermascope comprises an illumination polarizer configured to receive light from the plurality of light sources and transmit therethrough light having a first polarization state towards the skin. According to some example embodiments, the illumination polarizer is one of a linear polarizer or a circular polarizer. In an example embodiment, the dermascope comprises an imaging polarizer configured to receive light from the skin.

According to an example embodiment, the processor is configured to control illumination intensity of at least one light source in the plurality of light sources. In some example embodiments, the dermascope comprises multiple light sources having substantially the same spectral illumination characteristics, wherein the processor is configured to control the illumination by controlling output illumination of the multiple light sources individually or collectively. According to some example embodiments, the dermascope is implemented as part of a mobile electronic device. In certain example embodiments, the mobile electronic device is mobile phone or a tablet. In some example embodiments, the dermascope is implemented as part of a mobile electronic device that includes a camera lens, and the dermascope further includes an auxiliary optical system configured to be positioned in front of the mobile electronic device's camera lens or configured as a separate component that is in communication with the mobile electronic device. The auxiliary optical system includes one or more optical components to produce one or more of a particular: numerical aperture, field of view, spectral response or optical zoom capability for the dermascope. According to some example embodiments, the auxiliary optical system includes an achromatic doublet. In some example embodiments, the dermascope includes an auxiliary optical system configured to operate with a mobile electronic device and a portion of the dermascope that includes the at least one imaging sensor, the auxiliary optical system and the plurality of light sources is configured as a separate component from the mobile electronic device that is operable for positioning against the area of the skin, the separate component being in communication with the electronic mobile device, and the processor and the memory are integral parts of the mobile electronic device.

In an example embodiment, the dermascope includes an auxiliary optical system configured to operate with a mobile electronic device, and a portion of the dermascope that includes the auxiliary optical system and the plurality of light sources is configured as an attachable component to the mobile electronic device, and one of the at least one imaging sensor, the processor and the memory are integral parts of the mobile electronic device, wherein the attachable component is configured to attach to the electronic mobile device in such a way as to position the auxiliary optical system in front of, and in alignment with, the imaging sensor of the electronic mobile device. In another example embodiment, the dermascope includes an auxiliary optical system configured to operate with a mobile electronic device, a portion of the dermascope that includes the auxiliary optical system that includes a first one of the at least one imaging sensor is configured as an attachable component to the mobile electronic device, and a second one of the at least one imaging sensor, the processor and the memory are integral parts of the mobile electronic device. The attachable component can be configured to attach to the electronic mobile device in such a way as to position the auxiliary optical system in front of, and in alignment with, the second one of the at least one imaging sensor.

According to an example embodiment, the dermascope comprises an imaging annulus as part of the separate or the attachable component, the annulus having a side wall between a first end and a second end and forming a hollow interior between the first end and the second end, wherein the plurality of light sources and the imaging sensor are positioned proximate to the first end of the imaging annulus and the second end of the imaging annulus is adapted to be positioned against the skin such that when the imaging annulus is in contact with the skin, illumination of the area of the skin is predominantly due to the light produced by the plurality of light sources. One or both or the first or the second ends of the annulus can be open. In another example embodiment, the imaging annulus includes a transparent material that is positioned proximate to the second end of the imaging annulus to allow the annulus to be pressed against the skin and to thereby produce a substantially flat object plane. In some example embodiments, the imaging sensor includes two or more cameras that are configured to obtain images from the area of skin. According to some example embodiments, the processor is configured to produce one of more of the following based on images obtained from the two or more cameras: depth imaging information, autofluorescence information, three-dimensional images, images with differing resolution or images with differing magnifications. In certain example embodiments, the dermascope comprises one or more spectral filters to allow light of a particular spectral content to reach one or more of the cameras. In some example embodiments, the one or more filters include a long pass filter, a short pass filter, or a band pass filter. In an example embodiment, the dermascope comprises three cameras. In an example embodiment of the dermascope, one of the plurality of light sources is operable to emit radiation in an infrared range of wavelengths. According to an example embodiment, one of the plurality of light sources is operable to emit radiation in an ultraviolet range of wavelengths.

Another aspect of the disclosed embodiments relates to a method of imaging an area of a skin to determine a content of at least one chromophore in the skin, comprising: illuminating the area of the skin using a plurality of light sources having distinct spectral content to provide illumination in a plurality of distinct wavelengths or range of wavelengths where deoxyhemoglobin, oxyhemoglobin, or melanin exhibit differing optical characteristics; obtaining one or more images of the area of the skin; and processing information associated with the one or more images to obtain a level of at least one chromophore in the skin.

In some example embodiments of the method, processing the information comprises determining optical density values associated with two or more illumination wavelengths to quantify erythema. According to some example embodiments, the method further comprises converting a white-light image of the area of the skin into CIELAB color space and performing one or both of the following: (a) using lightness, L* to determine a relative measure of melanin content, or (b) using a direction of red color stimuli, a* as a measure of redness, wherein more positive values of the red color stimuli are indicative of higher levels of erythema.

Another aspect of the disclosed embodiments relates to a dermascope for imaging an area of a skin that incudes a plurality of light sources having different spectral contents and configured to illuminate the area of the skin, and at least one imaging sensor configured to detect light received from the area of the skin that is illuminated by the plurality of light sources. The dermascope further includes a processor and a memory comprising instructions stored thereon, wherein the instructions upon execution by the processor, cause the processor to: control illumination provided by the plurality of light sources to the area of the skin, and process information associated with the light detected by the at least one imaging sensor to produce images of the area of the skin. The illumination from the plurality of light sources is controlled to provide illumination in a plurality of distinct wavelengths or range of wavelengths that produce differing optical responses of the area of the skin. In one example embodiment, the produced images enable detection of a level of one or more chromophores in the skin, and the plurality of distinct wavelengths or range of wavelengths is selected to include two or more wavelengths at which at least two chromophores exhibit differing extinction coefficients.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

It is understood that the various disclosed embodiments may be implemented individually, or collectively, in devices comprised of various optical components, electronics hardware and/or software modules and components. These devices, for example, may comprise a processor, a memory unit, an interface that are communicatively connected to each other, and may range from desktop and/or laptop computers, to mobile devices and the like. The processor and/or controller can perform various disclosed operations based on execution of program code that is stored on a storage medium. The processor and/or controller can, for example, be in communication with at least one memory and with at least one communication unit that enables the exchange of data and information, directly or indirectly, through the communication link with other entities, devices and networks. The communication unit may provide wired and/or wireless communication capabilities in accordance with one or more communication protocols, and therefore it may comprise the proper transmitter/receiver antennas, circuitry and ports, as well as the encoding/decoding capabilities that may be necessary for proper transmission and/or reception of data and other information. For example, the processor may be configured to receive electrical signals or information from the disclosed sensors (e.g., CMOS sensors), and to process the received information to produce images or other information of interest.

Various information and data processing operations described herein may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media that is described in the present application comprises non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes Only a few implementations and examples are described and other implementations, enhancements and variations can be made based on what is described and illustrated in this patent document.

| Algorithm 1 Processing of reference images. |
| --- |

```
 1:   procedure ProcessReferenceImages (reference images)
 2:       for all reference images do
 3:           convert sRGB to linear RGB              ▷ Eq. (1)
 4:           if white-light image then
 5:               convert linear RGB to CIEXYZ       ▷ Eq. (2)
 6:           else if color image then
 7:               convert linear RGB to Yequal       ▷ Eq. (3)
 8:           end if
 9:           calculate luminance reference          ▷ Eq. (4)
10:           calculate illumination uniformity reference ▷ Eq. (5)
11:       end for
12:       return optical density reference images
13:       return illumination uniformity images
14:   end procedure
```

| Algorithm 2 Processing of dermal images. |
| --- |

```
1: procedure ProcessDermalImages (dermal images)
2:     for all dermal images do
3:         If USB camera then
4:             correct white-light image luminance  ▷ Eq. (8)
5:         end if
```

-continued

| Algorithm 2 Processing of dermal images. | | |
|---|---|---|
| 6: | convert sRGB to linear RGB | ▷ Eq. (1) |
| 7: | correct by illumination uniformity | ▷ Eq. (6) |
| 8: | if white-light image then | |
| 9: |    convert linearRGB to CIEXYZ | ▷ Eq. (2) |
| 10: |      convert CIEXYZ to CIELAB | ▷ Eqs. (17) and (18) |
| 11: | else if color image then | |
| 12: |    convert linear RGB to Yequal | ▷ Eq. (3) |
| 13: |    calculate optical density | ▷ Eq. (7) |
| 14: |    calculate melanin content | ▷ Eq. (19) |
| 15: |    calculate erythema | ▷ Eq. (20) |
| 16: |    solve chromophore concentration | ▷ Eq. (14) |
| 17: | end if | |
| 18: | end for | |
| 19: | end procedure | |

What is claimed is:

1. A dermascope for imaging an area of a skin, comprising:
   a plurality of light sources having different spectral contents and configured to illuminate the area of the skin;
   at least one imaging sensor configured to detect light received from the area of the skin that is illuminated by the plurality of light sources;
   a processor and a memory comprising instructions stored thereon, wherein the instructions upon execution by the processor, cause the processor to:
   control illumination provided by the plurality of light sources to the area of the skin, and
   process information associated with the light detected by the at least one imaging sensor to produce images of the area of the skin,
   wherein illumination from the plurality of light sources is controlled to provide illumination in a plurality of distinct wavelengths or range of wavelengths that produce differing optical responses of the area of the skin,
   wherein the dermascope includes an auxiliary optical system configured to operate with a mobile electronic device,
   wherein a portion of the dermascope that includes one of the at least one imaging sensor, the auxiliary optical system and the plurality of light sources is configured as a separate component from the mobile electronic device that is operable for positioning against the area of the skin, the separate component being in communication with the mobile electronic device, and
   wherein the mobile electronic device is integrated with a mobile electronic device processor and a mobile electronic device memory.

2. The dermascope of claim 1, wherein the processor is configured to determine an optical density value associated with two or more of the plurality of distinct wavelengths.

3. The dermascope of claim 1, wherein:
   the produced images enable detection of a level of one or more chromophores in the skin, the plurality of distinct wavelengths or range of wavelengths is selected to include two or more wavelengths at which at least two chromophores exhibit differing extinction coefficients, at a first of the two or more wavelengths, a first of the at least two chromophores has a higher molar extinction coefficient than a molar extinction coefficient of a second of the at least two chromophores, and at a second of the two or more wavelengths, the first of the at least two chromophores has a lower molar extinction coefficient than the molar extinction coefficient of the second of the at least two chromophores.

4. The dermascope of claim 3, wherein at a third wavelength, the first and the second of the at least two chromophores have substantially similar molar extinction coefficients.

5. The dermascope of claim 3, wherein the two or more wavelengths at which the at least two chromophores exhibit differing extinction coefficients correspond to two or more wavelengths at which that at least two chromophores exhibit two or more largest differences in their extinction coefficients.

6. The dermascope of claim 3, wherein the one or more chromophores include one or more of deoxyhemoglobin, oxyhemoglobin, or melanin.

7. The dermascope of claim 1, wherein the plurality of light sources includes a white light source.

8. The dermascope of claim 1, comprising an illumination polarizer configured to receive light from the plurality of light sources and transmit therethrough light having a first polarization state towards the skin, and an imaging polarizer configured to receive light from the skin.

9. The dermascope of claim 1, wherein the processor is configured to control illumination intensity of at least one light source in the plurality of light sources.

10. The dermascope of claim 1, further comprising multiple additional light sources having substantially same spectral illumination characteristics as one another, wherein the processor is configured to further control the illumination by controlling output illumination of the multiple additional light sources individually or collectively.

11. The dermascope of claim 1, wherein the auxiliary optical system includes an achromatic doublet.

12. The dermascope of claim 1, wherein the at least one imaging sensor includes two or more imaging sensors that are configured to obtain images from the area of skin, and wherein the processor is configured to produce one of more of the following based on images obtained from the two or more imaging sensors: depth imaging information, autofluorescence information, three-dimensional images, images with differing resolution, or images with differing magnifications.

13. The dermascope of claim 1, comprising one or more spectral filters to allow light of a particular spectral content to reach one or more of the at least one imaging sensor, wherein the one or more spectral filters include a long pass filter, a short pass filter, or a band pass filter.

14. The dermascope of claim 1, wherein at least one of the plurality of light sources is operable to emit radiation in an infrared range of wavelengths, or in an ultraviolet range of wavelengths.

15. A dermascope for imaging an area of a skin, comprising:
   a plurality of light sources having different spectral contents and configured to illuminate the area of the skin;
   at least one imaging sensor configured to detect light received from the area of the skin that is illuminated by the plurality of light sources;
   a processor and a memory comprising instructions stored thereon, wherein the instructions upon execution by the processor, cause the processor to:
   control illumination provided by the plurality of light sources to the area of the skin, and
   process information associated with the light detected by the at least one imaging sensor to produce images of the area of the skin, wherein illumination from the plurality of light sources is controlled to provide illumination in a plurality of distinct wavelengths or range of wavelengths that produce differing optical responses of the area of the skin, wherein the dermascope includes an auxiliary optical system configured to operate with a mobile electronic device, wherein a portion of the dermascope that includes the auxiliary optical system includes a first one of the at least one imaging sensor, and is configured as an attachable component to the mobile electronic device, wherein the mobile electronic device is integrated with a mobile electronic device processor, a mobile electronic device memory, and a mobile electronic device imaging sensor, and wherein the attachable component is configured to attach to the mobile electronic device in such a way as to position the auxiliary optical system in front of, and in alignment with, the mobile electronic device imaging sensor.

16. The dermascope of claim 1, comprising an imaging annulus as part of the separate component or an attachable component, the imaging annulus having a side wall between a first end and a second end and forming a hollow interior between the first end and the second end, wherein the plurality of light sources and one of the at least one imaging sensor are positioned proximate to the first end of the imaging annulus and the second end of the imaging annulus is adapted to be positioned against the skin such that when the imaging annulus is in contact with the skin, illumination of the area of the skin is predominantly due to the light produced by the plurality of light sources.

17. The dermascope of claim 16, wherein the imaging annulus includes a transparent material that is positioned proximate to the second end of the imaging annulus to allow the imaging annulus to be pressed against the skin and to thereby produce a substantially flat object plane.

18. The dermascope of claim 15, wherein the processor is configured to determine an optical density value associated with two or more of the plurality of distinct wavelengths.

19. The dermascope of claim 15, wherein:

the produced images enable detection of a level of one or more chromophores in the skin, the plurality of distinct wavelengths or range of wavelengths is selected to include two or more wavelengths at which at least two chromophores exhibit differing extinction coefficients, at a first of the two or more wavelengths, a first of the at least two chromophores has a higher molar extinction coefficient than a molar extinction coefficient of a second of the at least two chromophores, and at a second of the two or more wavelengths, the first of the at least two chromophores has a lower molar extinction coefficient than the molar extinction coefficient of the second of the at least two chromophores.

20. The dermascope of claim 19, wherein at a third wavelength, the first and the second of the at least two chromophores have substantially similar molar extinction coefficients.

21. The dermascope of claim 19, wherein the two or more wavelengths at which the at least two chromophores exhibit differing extinction coefficients correspond to two or more wavelengths at which that at least two chromophores exhibit two or more largest differences in their extinction coefficients.

22. The dermascope of claim 19, wherein the one or more chromophores include one or more of deoxyhemoglobin, oxyhemoglobin, or melanin.

23. The dermascope of claim 15, wherein the plurality of light sources includes a white light source.

24. The dermascope of claim 15, comprising an illumination polarizer configured to receive light from the plurality of light sources and transmit therethrough light having a first polarization state towards the skin, and an imaging polarizer configured to receive light from the skin.

* * * * *